United States Patent
Newman et al.

(10) Patent No.: US 12,117,408 B1
(45) Date of Patent: Oct. 15, 2024

(54) DEVICE FOR DETECTION OF CHEMICAL PROPERTIES OF A SAMPLE USING PARAMAGNETIC RESONANCE

(71) Applicant: Paramagnetix, Inc., Santa Cruz, CA (US)

(72) Inventors: Nathan Newman, Santa Cruz, CA (US); Saraansh Saxena, Santa Cruz, CA (US); Tian Xue, Santa Cruz, CA (US)

(73) Assignee: Paramagnetix, Inc., Santa Cruz, CA (US)

( * ) Notice: Subject to any disclaimer, the term of this patent is extended or adjusted under 35 U.S.C. 154(b) by 0 days.

(21) Appl. No.: 18/467,618

(22) Filed: Sep. 14, 2023

(51) Int. Cl.
*G01N 24/10* (2006.01)
*G01N 33/02* (2006.01)

(52) U.S. Cl.
CPC ............. *G01N 24/10* (2013.01); *G01N 33/02* (2013.01)

(58) Field of Classification Search
CPC ................................ G01N 24/10; G01N 33/02
See application file for complete search history.

(56) References Cited

U.S. PATENT DOCUMENTS

2020/0225378 A1* 7/2020 Godoy .................. G01N 24/10

FOREIGN PATENT DOCUMENTS

KR 101431011 B1 * 8/2014 ............. G01N 9/002

* cited by examiner

*Primary Examiner* — Jay Patidar
(74) *Attorney, Agent, or Firm* — Richard T. Black; Thomas J. Osborne, Jr.; FisherBroyles, LLP

(57) ABSTRACT

An electron paramagnetic resonant (EPR) instrument able to determine chemical properties of a sample using paramagnetic resonance is provided. In one embodiment, the instrument is able to measure the paramagnetic concentration of a wide variety of practical substances, ranging from food and beverages to biological specimens and solid-state electronic materials. The disclosed device can be portable and perform a measurement faster than commonly used techniques to quantify this parameter, including methods that use vibrating sample magnetometers and currently available electron paramagnetic resonance spectrometers.

23 Claims, 8 Drawing Sheets

DEVICE FOR DETECTION OF CHEMICAL PROPERTIES OF A SAMPLE USING PARAMAGNETIC RESONANCE

BACKGROUND

Food or environmental safety are important considerations in many situations. These include when food is prepared and provided for consumption at a restaurant, grocery store, home, or when the air in a building becomes contaminated. There are many potential sources of harm in either situation, including bacteria, toxins, contaminants, or particulate matter, as examples. Some of these substances are paramagnetic.

Paramagnetic species are atoms, molecules, and ions that have at least one unpaired electron. This category of chemical species includes (1) free radicals in which the unpaired electron(s) are in the outermost valence shell and (2) transition and rare-earth elements in which the unpaired electron(s) are in the partially filled d-electron and f-electron shells, respectively. Detecting free radicals is of particular interest because they are known to be harmful to human health if consumed in the air a person breathes or the food they eat. They can also be generated in the human body as byproducts of metabolism. Free radicals can also be formed in the body after exposure to toxins in the environment such as tobacco smoke or ultraviolet (UV) light. Free radicals are highly reactive and unstable molecules. Free radicals can damage DNA, sometimes causing mutations that can increase the risk of contracting a debilitating illness such as heart disease or cancer. Furthermore, the impingement of energetic light and/or particles can generate free radicals in a sample, allowing for the identification and quantification of a wide range of chemical substances of interest.

For this and other reasons, the detection (and in some cases the measurement of the number or concentration) of free radicals is of great interest to many industries, including food preparation and distribution, building environment control, and health professionals. Further, because free radicals may be generated during multiple stages of the manufacture, transport, and delivery of products, it would be beneficial to be able to identify, detect and/or measure the free radicals in a product when it is being delivered to an end user. This is particularly important for food served in a restaurant, as it may have been exposed to conditions that generate free radicals prior to it being served to a consumer. Also, irradiation with UV or high-energy particles can be used to generate free radicals so that an electron paramagnetic resonance instrument can identify the presence and even measure the concentration of a particular element, molecule, or ion.

The concentration and nature of paramagnetic species in a material can be characterized by measuring the difference in a sample's optical absorptivity in the presence and absence of an electron paramagnetic resonant magnetic field condition. Photon absorption can occur when the magnetic field strength is adjusted to cause a splitting in the electron(s) energy states (i.e., the Zeeman energy) with the energy difference between states equal to the energy of an impinging electromagnetic wave (i.e., the electron paramagnetic resonance condition where the spin flip or spin re-orientation process occurs).

Conventionally, the detection and/or measurement of free radicals is performed using a paramagnetic resonance machine or system. This provides a way to study the spectrum produced when a sample is subjected to suitable magnetic fields and irradiated with electromagnetic radiation, typically in the microwave region. While the use of the technique for spectroscopy is very beneficial (and shares many of the principles and uses of nuclear magnetic resonance (NMR)), such machines or systems are typically rather large, not portable, and relatively expensive. This makes them impractical for on-site use and hence for the detection of free radicals prior to end-user consumption or use. It also makes such systems impractical for detecting free radicals in environmental settings, such as buildings or offices.

Embodiments of the systems, apparatuses, and methods disclosed herein are directed at solving these and related problems individually and collectively.

SUMMARY

The terms "invention," "the invention," "this invention," "the present invention," "the present disclosure," or "the disclosure" as used herein are intended to refer broadly to all the subject matter disclosed in this document, the drawings or figures, and to the claims. Statements containing these terms do not limit the subject matter disclosed or the meaning or scope of the claims. Embodiments covered by this disclosure are defined by the claims and not by this summary. This summary is a high-level overview of various aspects of the disclosure and introduces some of the concepts that are further described in the Detailed Description section below. This summary is not intended to identify key, essential or required features of the claimed subject matter, nor is it intended to be used in isolation to determine the scope of the claimed subject matter. The subject matter should be understood by reference to appropriate portions of the entire specification, to any or all figures or drawings, and to each claim.

Embodiments are directed to a handheld device and system for the detection (and in some cases, the measurement) of free radicals, and their method of operation. The device is portable and relatively inexpensive compared to systems and devices used for spectroscopy applications, and therefore may be used to detect free radicals at sites or points of delivery of a product to an end-user. This allows the device to be used in hospitality situations to prevent food borne illness, in buildings to monitor air quality, and in other environments.

In one example embodiment, the disclosed and/or described handheld device may include the following elements, components, or structures:

A handheld and portable casing;
A cavity in the casing for insertion of a sample;
A dielectric resonator enclosed in a metal resonator cavity with a sufficiently low microwave resonator frequency, where the resonator and sample cavity form a resonator chamber;
  This allows the generation of the resonant magnetic field over a reasonably large volume (i.e., order of 0.1 to 1 $cm^3$) with one or more coin-size (or smaller) relatively strong permanent magnets, such as ceramic and Nd-based (NdFeB) magnets;
  In one embodiment, the dielectric has a relatively high dielectric constant material and is in the shape of a ring—this enables making the microwave resonator sufficiently small and able to have a relatively high microwave magnetic field and a reduced (relatively minimal) microwave electric field where the sample is positioned;
  To make accurate and sensitive electron paramagnetic resonance measurements, it is important that the difference in the quality factor (Q) of the resonator in the presence and absence of the resonant magnetic field condition be dependent upon the sample and not upon other components that comprise the resonator. In some embodiments, this condition has been achieved by ensuring that the following characteristics of the elements or components are satisfied:

The dielectric resonator, its holders and other insulating fixtures inside the metal enclosure have no or only a relatively minimal concentration of active paramagnetic species under the measurement conditions;

The metallic chamber enclosure, the magnetic-field coupling probe, and other conductive components enclosed or attached to the resonator cavity have no significant concentration of ferromagnetic components;

Under these conditions, the change in the quality factor (Q) between measurements made in the presence and absence of the resonant magnetic factor is almost entirely determined by the magnetic loss tangent of the sample;

In some embodiments, the metallic chamber enclosure may comprise the metal resonator cavity in which the sample resides. In alternate embodiments, the metallic chamber enclosure may comprise an outer enclosure for the entire device.

One or more permanent magnet(s) with an associated electromagnetic servo and a connecting shaft to enable the magnets to be physically moved into a desired position in a way to generate conditions needed to excite electron paramagnetic resonance within the sample;

The addition of a stationary electromagnet (typically in the form of a coil) can be used to precisely scan over small magnetic field regions or modulate the microwave response at very low frequencies (for noise rejection);

A miniature VNA (vector network analyzer on a printed circuit board) to measure the quality factor (Q) of the resonator at 2 or more DC magnetic field values;

Where in one embodiment, the VNA is programmed and operable to measure the reflection values of the resonator (i.e., the sample and containing chamber) and a reference signal to determine the reflection scattering parameter (S11) as a function of frequency through the resonator's resonance condition or value. The reference signal can be a short circuit or other means to create a signal that has a reflection coefficient of unity or near-unity. The value of S11 is determined by taking the ratio of the measured reflection from the device under test to that of a reference signal that reflects as close to 100% as possible at each frequency;

This permits a determination of the scattering parameter S11 values of the applied signal (the generated electromagnetic wave) in the presence of the sample as it goes through a paramagnetic resonance condition;

A loop-to-ground magnetic-field antenna connector (usually termed a magnetic-field coupling probe) positioned to excite the fundamental and higher order microwave resonator modes;

A suitable source of microwave energy to cause electron paramagnetic resonance in a sample and enable detection of free paramagnetic species when present in the sample;

One or more coaxial connectors and electrical wires that can be used to efficiently transmit the microwave signal between the microwave source and the magnetic-field coupling probe;

A microprocessor or controller programmed with a set of computer-executable instructions to cause the handheld device to perform one or more of the following operations, processes, or functions:

Measurement of a prepared sample placed into the cavity/resonator chamber to enable detection and/or identification of species of interest and to determine their concentration, when desired;

As examples, the sample may be prepared in several ways to achieve this desired outcome, including such techniques as (1) measuring the sample in its as-received state, (2) mixing the sample with a spin trap that reacts with short-lifetime radical species to generate a spin adduct that enhances the electron paramagnetic signal, (3) reacting the sample with enzymes or other chemical species that create a reaction product that can be detected, (4) exposing the sample to high energy radiation such as ultraviolet light or energetic particles, (5) other chemical or physical processes, or (6) a combination of one or more of the processes above;

Determination of the quality factor (Q) of the combined resonator chamber and sample when one or more permanent magnet(s) and/or electromagnetic coils are positioned so that the magnetic field value is not that needed for the electron paramagnetic electron resonance condition, where the Q value is determined using a vector network analyzer (VNA), and where this may comprise;

Selecting a set of RF frequencies (that typically fall in the microwave region of the spectrum) and corresponding LO (local oscillator) frequencies that scan through all or part of the combined resonance chamber and sample paramagnetic resonance condition;

In one embodiment, the LO frequency should satisfy the following conditions, $f_{RF}-f_{LO}=f_{IF}$, where IF is the intermediate frequency, and is typically on the order of 50 to 200 kHz;

Loading those values (the RF and LO frequencies) into a set of Phase Lock Loop frequency source registers and the subsequent generation of near-monochromatic microwave frequency radiation by the VNA and associated circuitry;

Using a directional coupler and a switch to direct the microwave radiation generated at the RF frequency to the resonator (i.e., the generated microwaves first goes through the directional coupler to a switch that directs the microwaves to either the resonator chamber and sample, or to a reference component or reference circuit);

Directing the signals through one or more amplifiers in series with the mixer (if needed to generate a sufficiently strong signal);

Achieving heterodyne detection by passing these signals through the mixer to attain an IF signal that is proportional to the magnitude of the reflected RF signal;

Filtering out undesired frequencies (including if desired, the sum frequency), while transmitting the IF difference signal to an Analog-to-Digital Converter (ADC);

Measuring the magnitude of the time-varying IF voltage by the ADC as a function of time for both the resonator (the cavity or chamber, sample) and a reference (i.e., a standard) using a common clock;

Using the resonator and reference data and suitable analysis to determine the S11 values as a function of frequency. The S11 values are comprised of a magnitude (which is the ratio of the amplitude of the IF voltage when measuring the resonator to that of the reference standard) and a phase (which is the difference in phase of the resonator's IF voltage compared to that of the reference signal). In one embodiment, this may comprise;

Fitting the S11 values using a Smith chart[1] to determine the quality factor (Q) of the resonator;

[1] The Smith chart is a graphical calculator or nomogram designed for electrical and electronics engineers specializing in radio frequency (RF) engineering to assist in solving problems with transmission lines and matching circuits. See Wikipedia entry for Smith chart.

Repeating one or more of the above steps or operations (as needed) from the step of "Selecting a set of RF frequencies and corresponding LO frequencies that scans through all or part of the resonator's resonance" to the step of "Fit the S11 values using a Smith chart to determine the quality factor";

One skilled in the art can fit the data points on the Smith Chart using a method such as that described by Kajfez (D. Kajfez, Artech House Inc. New York (2011);

An alternative is to calculate the quality factor (Q) using the equation $Q=f/\Delta f$, where f is the resonant frequency, and the peak width, $\Delta f$, is determined by the difference in frequency between the two 3 dB points located ±90 degrees from the resonant frequency point on the Smith Chart circle;

Determination of the quality factor (Q) of the combined resonator chamber and sample when one or more permanent magnet(s) and/or electromagnetic coils are positioned so that the magnetic field value is that needed to attain the electron paramagnetic electron resonance condition;

This will typically include following one or more of the steps or processes described for the out-of-resonance evaluation or measurement;

Subtract the determined quality factor for the off-resonance measurement from that for the on-resonance measurement to determine the change in the quality factor, which is proportional to the paramagnetic species in the sample;

From the change in quality factor in the two measurement situations, the magnetic loss tangent is determined, which is proportional to the concentration of paramagnetic species in the sample;

the magnetic loss tangent is an inherent property of a sample (i.e., it does not depend on sample's shape or size). When the magnetic loss tangent is determined, direct evaluation of the material's properties can be established independent of its size, shape, or measurement configuration. This allows direct comparison to other samples and can improve the accuracy and reliability of the measurement results;

In some embodiments, the difference in Q alone provides the magnetic loss tangent. In other embodiments, sample dimensions and/or fill factor are also taken into account to directly or indirectly to obtain magnetic loss tangent.

From prior calibration data (i.e., data obtained from samples for which the time since preparation and/or paramagnetic species concentration is known), evaluate the property of the sample being investigated, such as the estimated duration of time since the food or beverage was prepared or the amount of bacteria-generated toxins in the foodstuff.

The disclosed and/or described combination of features enables embodiments of the device to be made smaller and less expensive than conventional devices. As non-limiting examples, the relatively high microwave magnetic field where the sample is positioned along the central axis of the ring-shaped dielectric resonator facilitates a large EPR (electron paramagnetic resonance) absorption signal. The relatively small electric field where the sample is positioned provides a relatively high-Q factor (a figure of merit for resonator performance), even if the sample has high electric-losses because of the presence of electric dipole moments. This is important, as one does not want a Q degrading effect from a "lossy" sample (which, for example can be foodstuff or a biological specimen that can contain a significant fraction of water or other liquid).

Measurements of such "lossy" samples in standard commercial spectrometers are typically restricted to very small sample volumes, typically made with the sample enclosed in very narrow capillary tubes. This prevents the detection or quantification of low-concentration paramagnetic species in samples and corresponding high detection limits. A commercial manufacturer, Bruker, does offer a dielectric-loaded cavity design. However, such a design still restricts measurements of "lossy" samples to a relatively small size. The magnetic-field coupling probe efficiently excites and absorbs energy from the desired fundamental and higher microwave resonator modes of the dielectric resonator, helping to achieve the advantages and benefits of the disclosed device.

Conventional electron paramagnetic spectrometers operate their source, waveguides, attenuator, phase shifter, circulator, detector, amplifier, and directional coupler at microwave frequencies and don't use heterodyne detection. To gain additional sensitivity, a lock-in is also used. Such equipment is both bulky, heavy, and costly. Commercial electron paramagnetic systems from the most popular brands (e.g. Bruker and JEOL) currently cost in the range from ~$75,000 up to over $2,000,000.

In one embodiment, the quality factor (Q) is measured using a vector network analyzer circuit comprised of 2 microwave generators produced by phase-lock loops which are down-converted to an inter-frequency (IF) signal using a directional coupler, a high-frequency switch, a microwave mixer, and an amplifier, followed by processing the acquired signal using circuitry that includes an analog to digital (A-to-D) converter and a microcomputer and/or microprocessor. The magnetic loss tangent of the material or sample under test and its paramagnetic concentration can be inferred from the change in quality factor when a magnetic field is applied. If the magnetic field is varied between several or more points or values of magnetic field strength and/or the frequency of the impinging photons is varied, then the measurement process is termed electron paramagnetic resonance spectroscopy.

Embodiments of the disclosure are directed to systems, apparatuses, and methods for determining the magnetic loss tangent of a combined resonator and sample by measuring a change in quality factor of the combination under a condition of paramagnetic resonance and a condition of not being in paramagnetic resonance. From these measurements and determination of the magnetic loss tangent, the concentration of free radicals and other forms of paramagnetic species in a sample may be inferred. In one embodiment, a handheld device includes a resonator cavity/chamber into which a sample is inserted for evaluation. After insertion of the sample, the detection and/or measurement process proceeds by execution of the following steps, stages, functions, or operations:

- Determination of the quality factor (Q) of the combined resonator chamber and sample when one or more permanent magnet(s) and/or electromagnetic coils are positioned so that the magnetic field value is not that needed for the electron paramagnetic electron resonance condition;
  - where the Q value is determined using a vector network analyzer (VNA), and where this may comprise selecting a set of RF frequencies and corresponding LO (local oscillator) frequencies that scan through all or part of the combined resonance chamber and sample paramagnetic resonance condition;
  - Generation of near-monochromatic microwave frequency radiation by the VNA and associated circuitry;
  - Directing the microwave radiation generated at the selected frequencies to the resonator or to a reference component or reference circuit;
  - Using the resonator and reference data to determine the S11 values as a function of frequency and from that determine the quality factor (Q) of the resonator;
- Determination of the quality factor (Q) of the combined resonator chamber and sample when one or more permanent magnet(s) and/or electromagnetic coils are positioned so that the magnetic field value is that needed for the electron paramagnetic electron resonance condition;
  - This will typically include following one or more of the steps or processes described for the out-of-resonance evaluation or measurement;
- Subtract the determined quality factor for the off-resonance measurement from that for the on-resonance measurement to determine the magnetic loss tangent, which is proportional to the concentration of paramagnetic species in the sample;
  - In some embodiments, this difference in quality factor (for the off-resonance measurement from that for the on-resonance measurement) alone provides the magnetic loss tangent. In other embodiments, sample dimensions and/or fill factor are also taken into account to directly or indirectly to obtain magnetic loss tangent.
- From prior calibration data (i.e., data obtained from samples for which the time since preparation and/or paramagnetic species concentration is known), evaluate the property of the sample being investigated, such as the estimated duration of time since the food or beverage was prepared or the amount of bacteria-generated toxins in the foodstuff.

In one embodiment, the disclosure is directed to a system, apparatus, and method to detect and in some cases measure the concentration of paramagnetic species or free radicals in a sample. The system or apparatus may include a set of computer-executable instructions stored in a memory or data storage component (such as one or more non-transitory computer-readable media) and one or more electronic processors or co-processors. When executed by the processors or co-processors, the instructions cause the processors or co-processors (or a device of which they are part) to perform a set of operations that implement an embodiment of the disclosed method or methods.

Other objects and advantages of the systems, apparatuses, and methods disclosed will be apparent to one of ordinary skill in the art upon review of the detailed description and the included figures. Throughout the drawings, identical reference characters and descriptions indicate similar, but not necessarily identical, elements. While the embodiments disclosed or described herein are susceptible to various modifications and alternative forms, specific embodiments are shown by way of example in the drawings and are described in detail herein. However, embodiments of the disclosure are not limited to the exemplary or specific forms described. Rather, the disclosure covers all modifications, equivalents, and alternatives falling within the scope of the appended claims.

BRIEF DESCRIPTION OF THE DRAWINGS

Embodiments of the disclosure are described with reference to the drawings, in which:

FIGS. 2(f) and 2(g) show the magnitude and phase, respectively, of a resonator as a function of frequency as it is scanned through its resonance. FIG. 2(h) shows the corresponding Smith Chart.

DETAILED DESCRIPTION

Figure 1A:
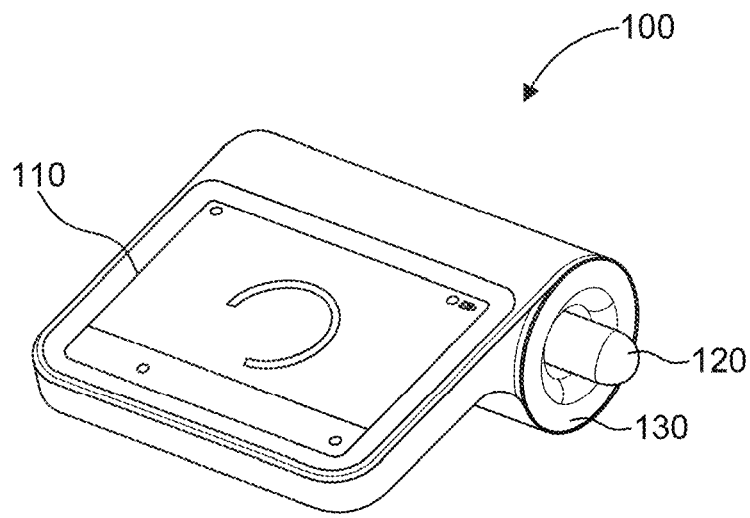
FIG. 1(a) is an illustration of an embodiment of the disclosed device for detecting and/or measuring the concentration of free radicals in a sample.

One or more embodiments of the disclosed subject matter are described herein with specificity to meet statutory requirements, but this description does not limit the scope of the claims. The claimed subject matter may be embodied in other ways, may include different elements or steps, and may be used in conjunction with other existing or later developed technologies. The description should not be interpreted as implying any required order or arrangement among or between various steps or elements except when the order of individual steps or arrangement of elements is explicitly noted as being required.

Embodiments of the disclosed subject matter are described more fully herein with reference to the accompanying drawings, which show by way of illustration, example embodiments by which the disclosed systems, apparatuses, and methods may be practiced. However, the disclosure may be embodied in different forms and should not be construed as limited to the embodiments set forth herein; rather, these embodiments are provided so that the disclosure will satisfy the statutory requirements and convey the scope of the disclosure to those skilled in the art.

Among other forms, the subject matter of the disclosure may be embodied in whole or in part as a system, as one or more methods, or as one or more devices. Embodiments may take the form of a hardware implemented embodiment, a software implemented embodiment, or an embodiment combining software and hardware aspects. For example, in some embodiments, one or more of the operations, functions, processes, or methods disclosed and/or described herein may be implemented by a suitable processing element or elements (such as a processor, microprocessor, CPU, GPU, TPU, QPU, state machine, or controller, as non-limiting examples) that are part of a client device, server, network element, remote platform (such as a Saas platform), an "in the cloud" service, or other form of computing or data processing system, device, or platform.

The processing element or elements may be programmed with a set of executable instructions (e.g., software instructions), where the instructions may be stored on (or in) one or more suitable non-transitory computer-readable data storage elements. In some embodiments, the set of instructions may be conveyed to a user over a network (e.g., the Internet) through a transfer of instructions or an application that executes a set of instructions.

In some embodiments, one or more of the operations, functions, processes, or methods disclosed herein may be implemented by a specialized form of hardware, such as a programmable gate array, application specific integrated circuit (ASIC), or the like. Note that an embodiment of the disclosed methods may be implemented in the form of an application, a sub-routine that is part of a larger application, a "plug-in", an extension to the functionality of a data processing system or platform, or other suitable form. The following detailed description is, therefore, not to be taken in a limiting sense.

Embodiments of the systems and methods disclosed and/or described herein are directed to a system, apparatuses, and methods for the detection and/or measurement of the magnetic loss tangent of a sample and to use that measurement to infer a concentration of paramagnetic species or free radicals in a sample. This capability may be used to monitor the state of a product prior to it being provided to an end user. This capability may also be used to monitor the condition or state of an environment, such as the air quality in a building or at a location.

As used herein, the following terms or phrases have at least the indicated meaning, but are not limited to:

Loss tangent; an inherent material property having both a magnetic and electric component. The magnetic and electric components are referred to as the magnetic loss tangent and electric loss tangent, respectively and their sum is equal to the loss tangent. The loss tangent quantifies a material's or circuit's dissipation when exposed to electromagnetic energy and is defined as $(w\varepsilon''+s)/(w\varepsilon')$ where w is the angular frequency and $\varepsilon''$ and $\varepsilon'$ are the real and imaginary part of the dielectric constant of a material or structure;

Magnetic loss tangent: the difference in the loss tangent values between when a paramagnetic sample is in a paramagnetic resonance condition and when it is not in that condition;

Resonator; a device that can absorb or emit energy at particular oscillation frequencies;

Free radical; an ion, atom, or molecule that contains one or more unpaired valence electrons;

Sample; a representative portion or a single item that is isolated, inspected or measured.

Quality factor, Q factor or Q: a dimensionless parameter that is defined as the ratio of the initial energy stored in the resonator to the energy lost in one radian of the cycle of oscillation and is equal to the ratio of a resonator's centre frequency to its bandwidth $f/\Delta f$ when subject to an oscillating driving force.

The presence of externally applied and internal magnetic fields causes a separation in the energy levels of unpaired electrons. This may be described by an electron paramagnetic spin Hamiltonian such as:

$$\mathcal{H}_{sp} = \frac{\beta_e}{h} B_0 g S + SDS + SAI - g_n \frac{\beta_n}{h} I B_0 + I N_{qt} I$$

where $\beta_e$ is the Bohr magnetron;

h is Planck constant;

$B_o$ is the static (or quasi-static field when a slow variation (compared to a microwave field) is applied). It is referred to as the static field herein;

g is the g-factor;

S is the magnetic moment of the unpaired electron (or electrons);

D is the traceless zero-field interaction or fine structure tensor;

A is the hyperfine interaction matrix;

I is the nuclear spin quantum number;

$g_n$ is the nuclear g-factor;

$\beta_n$ is the nuclear magnetron; and $N_{qt}$ is the traceless nuclear quadrupole tensor.

As indicated by the above equation, the energy level(s) of an unpaired electron are separated by an external magnetic field, with the amount of separation being (to a first approximation) proportional to the magnetic field strength. This separation enables absorption and re-emission of photons which are used as part of the disclosed process to measure a change in the Q factor of the combined resonator chamber and sample, and from that the concentration of paramagnetic species in the sample. The determination of the loss tangent and magnetic loss tangent can be an intermediatory step and has the advantage that these values are inherent properties and do not depend on the shape or size of the sample and can thus be directly compared to the results from other types of instruments.

In one embodiment, the external magnetic field used to cause the separation of the electron energy levels as a result of the electron spin alignment in the applied magnetic field is formed using one or more permanent magnet(s) and/or electromagnet(s) with specific configuration and characteristics. These characteristics may include one or more of:

A sufficiently large volume where a sample can reside (of order 0.1-0.5 cm$^3$) and be in a resonance condition as a result of the external magnet field design and presence of a ring-shaped dielectric resonator with a relatively high dielectric constant;

This enables the realization of higher signal-to-noise ratios resulting from the increased signal resulting from (a) the use of larger samples (and thus more unpaired electrons), and (b) enhanced microwave magnetic-field intensities over a larger region of space;

The ring-shaped dielectric resonator assists in creating a relatively large volume where the sample can reside and have a very small component of the microwave electric field. This prevents the degradation of the Q value by the dipolar absorption of microwaves by the sample (as in heating of water and foodstuff in a microwave oven). The signal is proportional to the resonator Q.

When the electron paramagnetic resonance condition is satisfied, an unpaired electron can absorb a photon of energy hv, where h is Planck's constant and v is the photon frequency. In this situation:

the photon energy hv can result in a spin flip and/or a spin reorientation of coupled electrons;

further, due to the Maxwell-Boltzmann distribution factor, the relative population of the lower states will be greater than the upper states when in equilibrium or near-equilibrium (i.e., for small photon intensities when the transition between levels is not fully saturated).

In one embodiment, a sample (e.g., food, gas, liquid, or a combination) is placed into a cavity of the disclosed handheld device. The cavity is part of a resonator chamber into which energy is coupled to the disclosed loop that is part of the magnetic-field coupling probe, also referred to as the launch connector. In one embodiment, the resonator chamber is constructed of components that create a relatively high magnetic field when excited by microwave radiation, and a corresponding relatively low electric field in the sample. A vector network analyzer is used as part of a process to measure the quality factor (Q) of the resonator (which comprises both the sample and the chamber containing the sample) at two or more DC magnetic field values, by scanning (i.e., generating impinging photons) at one or more frequencies.

The sample is irradiated with microwave radiation at a frequency, v, where v and B$_0$ are chosen or related as indicated by the spin Hamiltonian, a suitable approximation, or from earlier experimental measurements;

In one example, the microwave radiation is carried through a coaxial connector or wire and then launched using a magnetic-field coupling probe in the form of a wire loop coupled to ground and in which a current is flowing to be able to critically or near-critically couple to one or more desired resonant dielectric modes (typically the fundamental mode);

The static magnetic field created by the permanent magnet or magnets may be varied until the difference between the two energy levels of the unpaired electron(s) in the sample matches the energy of the impinging photons; this defines the electron paramagnetic resonant condition.

By absorbing the impinging photons, the unpaired electrons absorb the microwaves when the electron paramagnetic condition is satisfied, increasing the loss in the combined resonator chamber and sample, and decreasing the quality factor. The difference in the quality factor is determined when the magnetic field value is at the electron paramagnetic resonance conditions and when it is not. This may then be used to determine the level of electron paramagnetic resonant absorption and the relative number of unpaired electrons in the sample. By taking the difference of the quality factor while in a resonance condition and when out of the resonance condition at very closely spaced times to determine the magnetic loss tangent, the influence of systematic errors in the (1) determinations of the VNA microwave calibration parameters and resonator coupling value, (2) fitting algorithms, and/or (3) impedance mismatch are significantly reduced and, in many cases, virtually eliminated.

The change in the Q factor during the measurement process (which is a measure of the resonator chamber and sample response) is used to generate a value for the paramagnetic electron content of the sample (i.e., the number of "unpaired" electrons) through its relationship to the difference in quality factor or the magnetic loss tangent. In one embodiment, the disclosed device comprises an electromagnetic resonator that includes a relatively high-dielectric constant dielectric to confine the electric field within the dielectric, and thus largely away from where the sample is placed. The size and materials used for the enclosed metallic chamber enclosure were designed to minimize or eliminate radiation, radiation-like, and near-field losses and still be able to be manufactured at a moderate cost. This enables the achievement of a high-performance resonator with a relatively high quality (Q) factor during measurements.

Because of the relatively high dielectric constant of the ring-shaped dielectric inside the metal cavity (where the cavity is comprised of an outer metal enclosure and the resonant chamber in which a sample is placed), the modes of that resonator are shaped (and behave) like modes of an isolated ring-shaped dielectric. The metallic chamber enclosure prevents radiation losses (which may be large in its absence). During the measurement process, there is a small amount of microwave electric field and microwave magnetic field components on the outer enclosure walls, so there is some loss (termed near field loss) causing a small degradation in Q, but not enough to create a measurement problem if the cavity size is chosen carefully. Dielectric resonator cavities are typically made to be ~3 times the size of the dielectric, but the combination of very high dielectric constant and low loss tangent dielectric facilitates the use of high-quality material in a compact resonator with a cavity on the order of 30% larger than the dielectric. It is also desirable that the microwave magnetic field be sufficiently large, especially in the sample volume, as this condition maximizes the EPR absorption process under a resonant condition.

In contrast to conventional spectroscopy approaches based on paramagnetic resonance, embodiments are designed to quantify the loss tangent of the microwave resonator and magnetic loss tangent of the sample and use that to infer the concentration of paramagnetic species in the sample and not to perform high-resolution EPR spectroscopy by generating a more complete spectrum. In some embodiments, this is accomplished by measuring the Q factor (to determine a change in Q factor as a sample passes through a resonance condition) of a resonator comprised of a resonator chamber and sample at one or more specific magnetic field values or through a range of magnetic field values to quantify the concentration of the paramagnetic species present, or in some use cases only species from a particular chemical element, molecule, or ion.

Because the magnetic-field dependence of the energy states in the spin Hamiltonian depends on both the nature of the paramagnetic species and the local chemical/species environment, the choice of one or more magnetic field values can be used to not only distinguish between species, but in some cases to independently quantify each of their concentrations.

For example, even though the impurity atoms, such as $Mn^{2+}$, $Fe^{3+}$, and $P^0$ impurities in MgO, $Al_2O_3$, and Si, respectively, all have g=2 resonant peaks, they can be distinguished from each other because of the different hyperfine interactions and the resulting differences in the magnetic field values for the hyperfine peaks. $Mn^{2+}$ and $Fe^{3+}$ with a nuclear moment of 5/2 will both have 6 hyperfine peaks at different magnetic field strengths, but their spacing will differ. $P^0$ with its nuclear moment of ½ will have 2 hyperfine peaks at different magnetic field strengths.

In one embodiment, microwave energy is introduced into the resonator cavity using the disclosed magnetic-field coupling probe which is connected to a source of microwave radiation. This type of magnetic-field coupling probe consists of a loop that terminates in a ground connection and is very efficient at launching and detecting a microwave magnetic field. It thus couples strongly to microwave modes that have a high magnetic field component in the location of the connector, such as the fundamental mode of a TE01δ of a ring-shaped dielectric resonator. The same connector is used to couple to and transmit some of the reflected signal of the resonator whose Q is affected by the paramagnetic electrons' transitions. A coaxial connector and wire can be used to efficiently transmit the microwave signal between the microwave source through the microwave coupler to the magnetic-field coupling probe.

As disclosed and/or described, the VNA is both the source and the instrument that measures both the intensities and phases of the outgoing and incoming signal. The ratio of the incoming signal divided by the outgoing signal and their difference in phase is (by definition) the complex scattering parameters S11.

The VNA measurements enable the determination of the S11 parameters as it sweeps the frequency through the microwave resonator's resonance condition, allowing for the determination of the quality factor when the sample is under electron paramagnetic resonance conditions and when it is not. This allows for the direct determination of the magnetic loss tangent of a sample. This can be compared to the conventional approach where an investigator measures the derivative of reflection at a specific frequency as a function of magnetic field strength as part of determining a full(er) or complete spectrum of a sample. Since the quality factor of the resonator cannot be determined from measurements at a single frequency, this technique cannot directly determine quantitative loss tangent values without additional information. Thus, researchers using the conventional approach typically compare their unknown sample's results to a standard measurement sample with a known concentration of paramagnetic species to make quantitative determinations.[2] This requires acquiring an expensive standard with similar concentrations and properties and making multiple measurements.

[2] Note that since the conventional approach does not determine the magnetic loss tangent, knowledge of the lifetime will not allow it to calculate the paramagnetic concentration independently. In contrast, because the disclosed approach does determine this quantity, it just needs to make a measurement of the magnetic loss tangent and then know T1 (unsaturated) or T2 (saturated) to calculate the desired value with reasonable accuracy (and both T1 and T2 if it is desired to be precise if the sample is partially saturated).

There have been efforts to make quantitative measurements with conventional methods without a standard by measuring the quality factor at zero field along with the derivative of the reflection values at the resonant frequency. However, since the quality factor is not directly measured under the electron paramagnetic resonance condition, this indirect method necessitates making several undesirable approximations and is not as convenient or accurate as desired for many use cases.

As mentioned, the concentration and type of paramagnetic species in a material can be characterized by measuring the difference in optical absorptivity in the presence and absence of a magnetic field. The underlying concept is that the magnetic loss tangent[3] (and absorptivity) increases when a material's electron(s) are in the electron paramagnetic resonant condition. This is because the energy of a microwave photon causes a spin flip or spin reorientation of the electrons. When this occurs, both the microwave (optical) absorptivity and magnetic loss tangent increase. Through extensive experimentation and analysis, the inventors have discovered that while the loss tangent characterization is an inherent property of the material (i.e., does not depend on size or shape), the definition of absorptivity has several meanings, and may be subject to ambiguity. For this reason, the inventors have discovered that determining and interpreting a loss tangent value may be preferable to considering absorptivity when characterizing a sample.

[3] The loss tangent (tan (δ)) is a measure of signal loss due to the inherent dissipation of electromagnetic energy by an element or component. The dielectric loss tangent (tan δ) of a material denotes quantitatively dissipation of the electrical energy due to different physical processes such as electrical conduction, dielectric relaxation, dielectric resonance, and loss from non-linear processes. The quality factor Q is the reciprocal of dielectric loss tangent; Q=1/tan δ. The magnetic loss tangent is the difference in the loss tangent values between when the sample is in a paramagnetic resonance condition and when it is not in that condition.

In one embodiment, to implement this type of measurement process in a compact form, the magnetic loss tangent for a sample measured both in and not in the electron paramagnetic condition can be determined by measuring the quality factor (Q) of a microwave dielectric resonator in magnetic fields created by a movable permanent magnet. Based on extensive modeling using Maxwell-equation simulations and experimentation related to this disclosure, the inventors determined that the specific combination of a cylindrical or ring dielectric with a relatively large dielectric constant and small loss tangent, particularly the magnetic loss tangent, in combination with the use of coin-sized permanent magnets has an unexpected result of allowing the construction of a hand-held device that is sensitive enough for a wide range of practical applications and can be produced at a far lower cost than conventional electron paramagnetic resonance spectrometers.

In one embodiment, the disclosed vector network analyzer (VNA) scans through one or more monochromatic frequencies and measures the reflected signal at each frequency. The amplitude and phase of the reflected signal for the resonator and standard are measured as a function of frequency (typically between 1.80 to 1.84 GHZ, which is in the microwave region) to determine the S11 values. By determining the center-frequency, and width of the resonance peak and then performing a suitable analysis, it is possible to determine the quality factor and infer the loss tangent of the sample.

The Q of the resonator can be determined from the Smith chart by fitting the circle using the standard method described in the book "Q Factor Measurements Using MAT-LAB" (D. Kajfez, Artech House Inc. New York (2011)). Another method involves using the equation Q=f/Δf for the S11 resonance peak, where f is the resonant frequency and Δf is the difference in the frequency between the 3 dB points which are located at ±90 degrees from the resonant frequency on the Smith chart. Another simple analysis can be made by assuming that there is no loss in the system. With this assumption, the scattering parameter $S_{12}$ can be inferred from the determined S11 values as a function of frequency using the relation $S11^2+S12^2=1$. Then the loss tangent can be inferred from the S12 values by dividing the central resonant frequency, f, by the peak width Δf (i.e., f/Δf) which corresponds to the frequencies that fall 3 dB below the maximum value of the peak at resonance.

As mentioned, the magnetic loss tangent is used to infer or deduce the concentration of free radicals in the sample. Under conditions in which losses in the sample dominate the resonator losses, to a first approximation, the loss tangent of the sample can be obtained by taking the inverse of the product of the fill factor times the measured quality factor, where the fill factor is defined as the ratio of the sample volume to the metal enclosure cavity volume.

Under conditions when dielectric losses and/or near fields contribute a significant amount to losses, the loss tangent of the sample can be estimated with reasonable accuracy by the following equation:

$$\text{loss tangent}_{sample}=1/\text{fill factor}\times(1/Q_{measured}-\text{loss tangent}_{dielectric}-\text{loss tangent}_{near\text{-}field\ losses}),$$

where loss tangent$_{sample}$ is the loss tangent of the sample;
$Q_{measured}$ is the measured unloaded quality value of the resonator and sample combination;
loss tangent$_{dielectric}$ is the loss tangent of the dielectric; and
loss tangent$_{near\text{-}field\ losses}$ is the effective loss tangent of the near-field losses.

A microwave engineer skilled in the art can make measurements to determine the parameters on the right of the equation symbol, although the fill factor could potentially be more easily determined using commercial equipment solvers (e.g., HFSS by Ansys and the CST Suite by Mathworks).

For more accurate determinations of the various terms in the above equation, electromagnetic simulations can be performed using the geometry of the resonator and its contents along with the known quantities of the loss tangent of the dielectric resonator material and other dielectric components, and the surface resistance of the metal cavity walls. Commercial software (such as HFSS by Ansys and the CST Suite by Mathworks) can be used by those skilled in the art to perform a more accurate determination of the loss tangent of a sample.

By measuring the changes in the quality factor (Q) of a sample and resonator chamber placed near a microwave dielectric resonator[4] in the presence and absence of a magnetic field whose value satisfies the electron paramagnetic condition, the differences in the loss tangent of the sample can be inferred with precision and the magnetic loss tangent of the sample and the concentration and the nature of a paramagnetic species can be determined. As described herein, the determination of the concentration of a paramagnetic species may involve consideration of other factors, such as knowledge of the sample's $T_2$ (termed the spin-spin or transverse relaxation time) and/or $T_1$ (termed the spin-lattice or longitudinal relaxation time) in combination with the Bloch equation[5] to infer the paramagnetic concentration from the magnetic loss tangent.

[4] The modes for the resonator are almost completely determined by the microwave dielectric. In embodiments, the electric field is almost all inside the dielectric. So, it is termed a dielectric resonator, even though it has an enclosure. This is different than a dielectric-loaded resonator where the dielectric helps to confine some fields, but the modes are similar to that of the external cavity.

[5] The Bloch equation(s) are a set of macroscopic equations used to calculate the nuclear magnetization M=(Mx, My, Mz) as a function of time when relaxation times T1 and T2 are present.

The disclosed approach has multiple advantages over devices and techniques that are conventionally used to perform electron paramagnetic spectroscopy. The instruments used to perform these experiments are almost entirely located in research labs. The disclosed approach is quantitative and benefits from averaging both (a) the IF signal data with typically many hundreds of points to determine the S11 value at each frequency, and then (b) using both the angle and phase information over multiple frequencies, typically on the order of 50, to collectively determine an accurate measurement of a resonator quality factor.

In contrast, the conventional approach applies a small, time-varying magnetic field, referred to as the modulation, in addition to sweeping a larger "static or quasi-static" magnetic field at the single resonant frequency with a microwave detector. A lock-in amplifier is used to measure the output, resulting in a single value for the time derivative of the reflected signal at each magnetic field value. Despite the limited use of averaging, the frequency selectivity and almost complete rejection of noise outside the modulation frequency (as a result of the use of the lock-in amplifier) provide a relatively sensitive method of measurement.

While both the disclosed device and conventional techniques can both provide useful information, the conventional method's requirement to use bulky microwave components, advanced lock-in electronics and a resonator with a sufficiently high-quality factor (e.g., over ~2,500) has proven to be a barrier that has prevented the commercialization of a hand-held, quantitative electron paramagnetic resonance instrument.

FIG. 1(a) is an illustration of an embodiment of the disclosed device 100 for detecting and/or measuring the concentration of paramagnetic species in a sample. As shown in the figure, the embodiment includes a touch screen user interface or display 110, a sample insertion tool 120, and a cavity 130 into which the tool is inserted when performing a measurement. Cavity 130 forms part of a resonator chamber used to detect and/or measure the paramagnetic species in the sample.

Figure 1B:
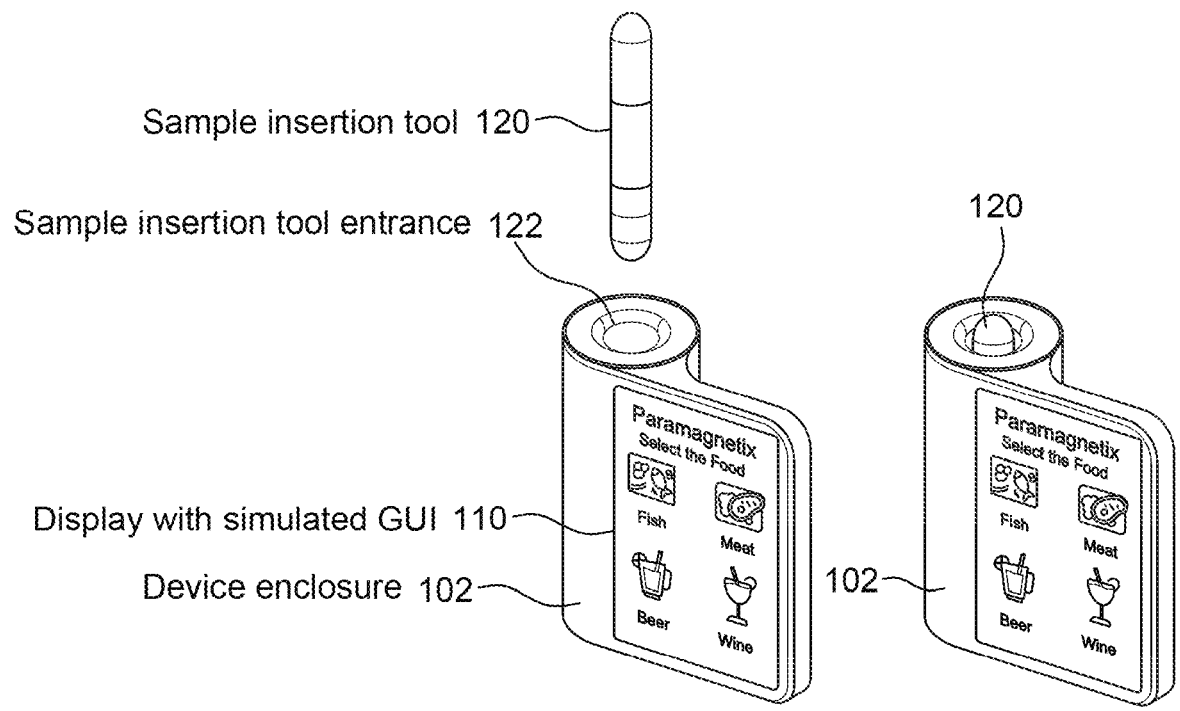
FIG. 1(b) is another view of the components or elements illustrated in FIG. 1(a)

FIG. 1(b) is another view of the components or elements illustrated in FIG. 1(a). This figure illustrates the sample insertion tool 120, the tool entrance to the cavity 122, the device enclosure 102, and a simulated user interface (GUI) display 110. In one embodiment, the display 110 may include one or more icons representing what is to be measured, such as icons for fish, chicken, coffee, a beverage, and other (these may correspond to pre-programmed measurement or operational parameters or values).

Once a type of sample to be tested is chosen, a button appears that says "test". Once the test button is selected and the test is completed, the evaluation for fish and chicken can be expressed (as non-limiting examples) as "very fresh", "fresh", "edible", and "non-edible". For coffee, the evaluation for coffee might indicate "over roasted", "slightly over roasted", "ideal roasting", "slightly under roasted", or "under roasted" (again, as non-limiting examples). For a beverage, it could indicate either "safe" or "dangerous" (as non-limiting examples). For other, it can display a quantitative determination of the number of paramagnetic species in the sample. The display can also record which user is making the measurement, the time and date, and the measurement result. There may also be an option to get to a diagnostic feature to test if the electronics and interface are working up to the original specification.

Figure 1C:
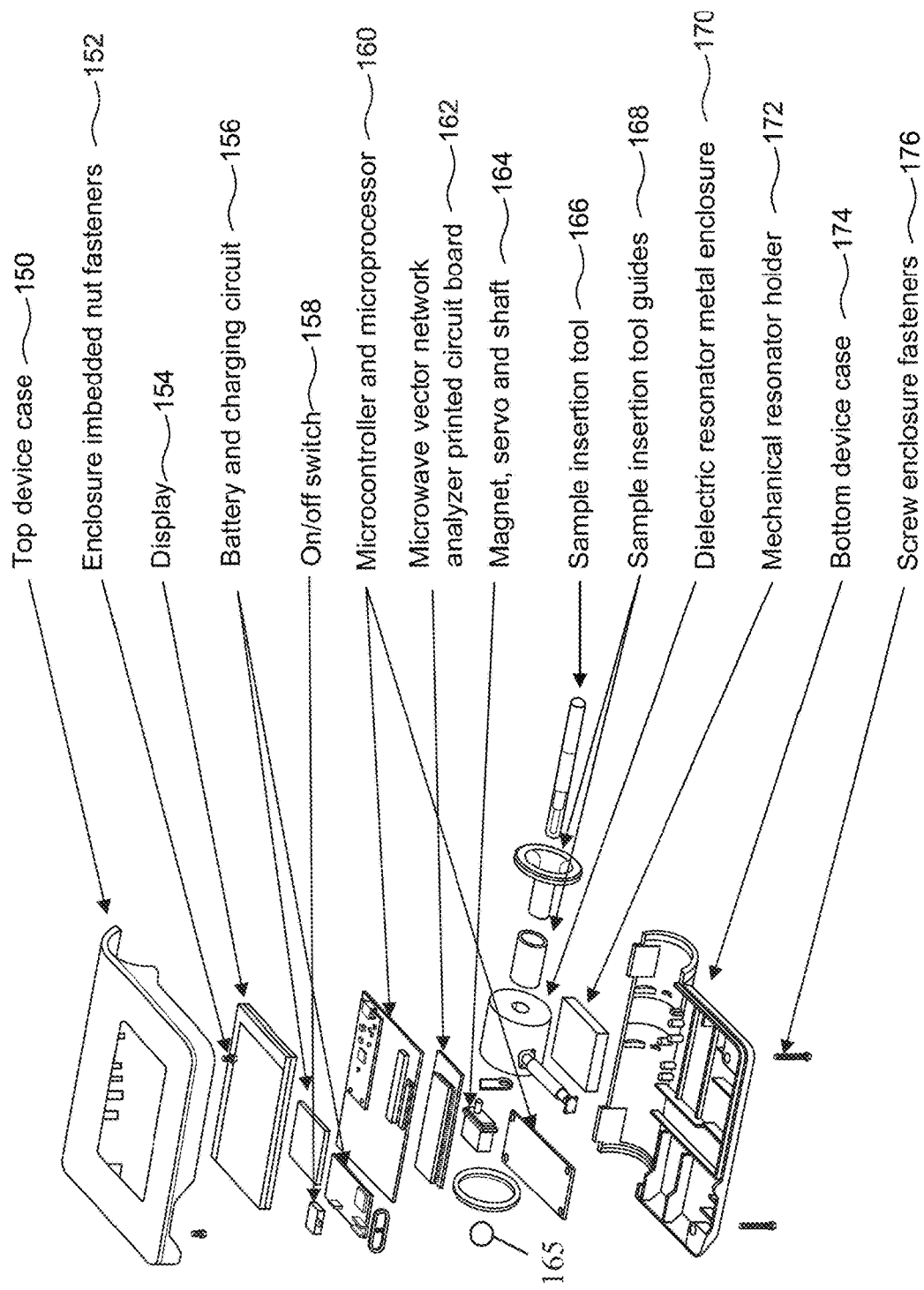
FIG. 1(c) is a diagram illustrating an exploded view of the components or elements of the embodiment of the disclosed device shown in FIG. 1(a)

FIG. 1(c) is a diagram illustrating an exploded view of the components or elements of the embodiment of the disclosed device shown in FIG. 1(a). As shown in the figure, in one embodiment the disclosed device may include the following:
A top of the device case 150;
One or more embedded fasteners 152;
A display (typically a panel) 154;
A battery and associated charging circuit 156;
An on/off switch 158;
A microcontroller and microprocessor, typically on a printed circuit board (PCB) 160;
A microwave vector network analyzer (VNA) typically implemented on a printed circuit board 162;
A magnet, servo, and shaft that form part of the resonance cavity 164;
Electromagnet(s) 167
A source of irradiation configured to generate unpaired electrons in the sample 165;
A sample insertion tool 166;
One or more guides for the sample insertion tool 168;
A dielectric resonator enclosure (metal) 170;
  A ring-shaped dielectric positioned inside the dielectric resonator enclosure (not shown);
A mechanical resonator holder 172;
A bottom of the device case 174; and
One or more screws or fasteners to attach the top to the bottom of the device case 176.

Figure 2A:
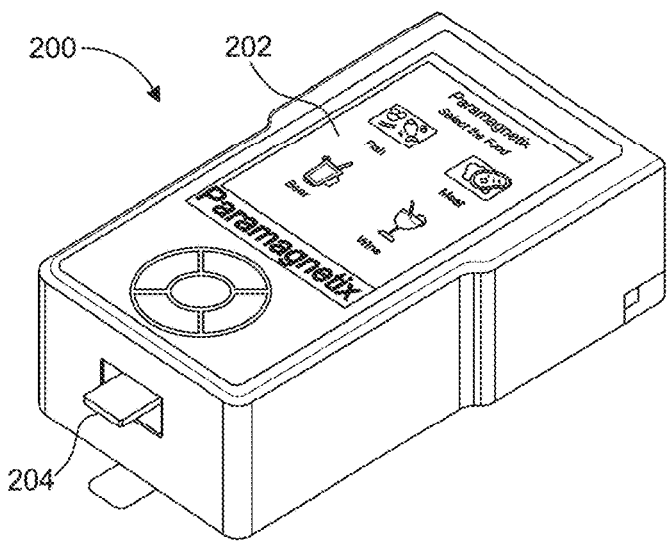
FIG. 2(a) is an illustration of a second embodiment of the disclosed device for detecting and/or measuring the concentration of free radicals in a sample.

FIG. 2(a) is an illustration of a second embodiment of the disclosed device 200 for detecting and/or measuring the concentration of free radicals in a sample. As shown in the figure, this embodiment similarly includes a user interface or display 202 and a sample insertion tool 204.

Figure 2B:
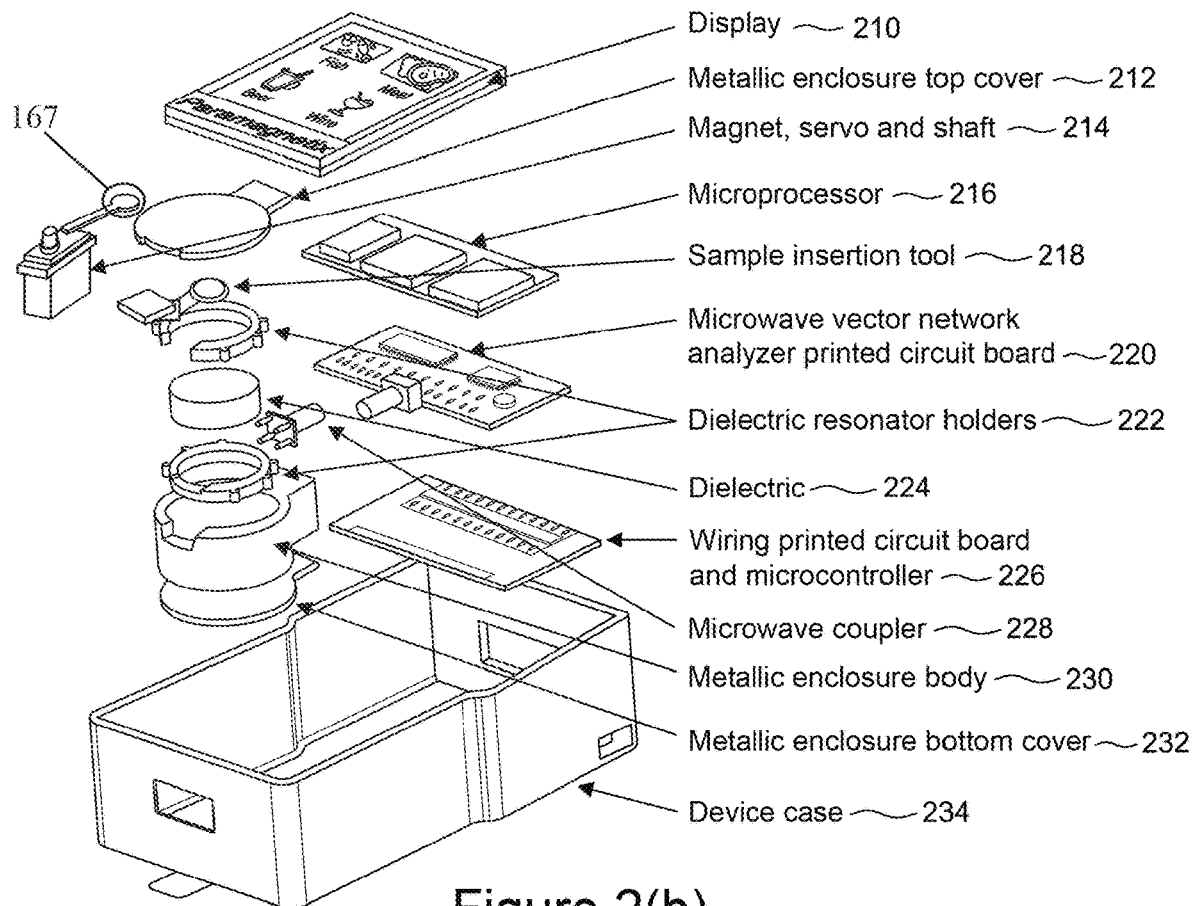
FIG. 2(b) is a diagram illustrating an exploded view of the components or elements of the embodiment of the disclosed device shown in FIG. 2(a)

FIG. 2(b) is a diagram illustrating an exploded view of the components or elements of the embodiment of the disclosed device shown in FIG. 2(a). As shown in the figure, in one embodiment the disclosed device may include the following:
display 210;
A metallic chamber enclosure top cover 212;
A magnet, servo, and shaft 214;
Electromagnet(s) 167
A microprocessor 216;
A sample insertion tool 218;
A microwave frequency vector network analyzer (VNA) printed circuit board 220;
One or more dielectric resonator holders 222;
A dielectric 224;
A wiring printed circuit board and microcontroller 226;
A microwave directional coupler 228;
A metallic chamber enclosure body 230;
  A ring-shaped dielectric positioned inside the metal enclosure (not shown);
A metallic chamber enclosure bottom cover 232; and
A device case 234.

In some embodiments, the dielectric and the mechanical resonator holder 172 shown in FIG. 1(c) and the dielectric and the one or more dielectric resonator holders 222 shown in FIG. 2(b) have a paramagnetic concentration below $10^{15}$/cm$^3$ or below 1018/cm$^3$. In other embodiments, the mechanical resonator holder 172 shown in FIG. 1(c) and the one or more dielectric resonator holders 222 shown in FIG. 2(b) are made of plastics such as polyactic acid (PLA).

As mentioned, by determining the change in the quality factor (Q) of a sample and resonator chamber that are part of a microwave dielectric resonator in the presence and absence of one or more electron paramagnetic resonance inducing magnetic fields, the difference in the loss tangent of the sample can be inferred with precision to derive the magnetic loss tangent, and from one of those values, an estimated concentration and nature of a paramagnetic species (such as free radicals, a transition metal element, or a rare-earth element) in the sample. However, in some cases, this may not provide sufficient measurement accuracy.

In such situations, increased measurement accuracy can be attained by scaling the results to measured changes in the response from a reference or standard sample. Increased accuracy may also be obtained by using first principles, in which electromagnetic simulations of the dielectric resonator structure and sample can be used to directly determine the sample's absorptivity and loss tangent from the quality factors measured under the resonance conditions. In general, measurement accuracy is highest for a reflection measurement if (a) the quality factor of the resonator is relatively high, (b) the microwave power is relatively high (but not high enough to cause saturation), (c) the resonator is critically coupled, and (d) the sample, microwave magnetic field intensity, and the tangential resonant DC magnetic field overlap to the greatest degree feasible.

In some embodiments, the desired combination of measurement conditions was obtained by the development of a small (<2" diameter, <1.5" height) high-quality factor enclosed resonator that could operate in the 1.5-3 GHz microwave region. The internal components of the resonator included a high dielectric constant (>75) ring-shaped resonator and mechanical support material with both low microwave loss (preferably a loss tangent <$10^{-5}$) and a relatively small paramagnetic center concentration (i.e., a very small magnetic loss tangent, preferably <$5\times10^{-5}$). Using this configuration, very high Q values (the unloaded Q being >5,000, and the loaded Q being approximately 2500) were obtained with minimal dielectric to enclosure spacings[6]. This was unexpected and surprising given that relatively large microwave magnetic fields extended outside the dielectric and onto the enclosure walls. This configuration in combination with the use of one or more coin-sized (e.g., cylinder, ring and/or square) permanent magnets was used to create an EPR resonant condition over a sufficiently large volume and enabled a quantitative measurement of the paramagnetic defect concentration of a species of interest.

[6] The unloaded Q is for weak electromagnetic coupling and the critically coupled (i.e., optimally loaded) Q is less and turns out to be half for critical coupling.

In one embodiment, for example, a resonator is less than 1.5" in diameter and 0.95" in height and has an unloaded quality factor over 4,000 and a critically coupled quality factor over 2,000.

In one embodiment, the device has dimensions of less than 12"×12"×12" or less than 8"×8"×5".

In contrast to conventional EPR, which is performed in a spectroscopic mode with very precise control of the magnetic field as it scans to obtain a spectrum, the disclosed device is used to determine the paramagnetic concentration of a particular sample with known electron paramagnetic resonance spectra. In this way, embodiments can identify critical magnetic field values in the spectra and their relative ratios so that certain chemicals and their concentrations can be uniquely identified.

This allows for more rapid measurements. And, because high resolution scans over a wide range contain regions that aren't used in the analysis, in a significant number of cases the use of carefully designed sampling techniques can be used to identify chemicals and make quantitative measurements with the same level of confidence as taking a higher resolution scan.

Work being conducted by the inventors includes actively building a library of electron paramagnetic spectra for materials of interest and using that knowledge to design measurement parameters so that the disclosed device can detect the presence and, when desired, determine the concentration of a specific paramagnetic species. For example, this enables using a measurement of the EPR signal at two magnetic field values or points, for example at 0 and 680 Gauss (or at a few points such as a measurement at 321 and 642 Gauss, corresponding to g=2 and g=4 at a measurement frequency of 1.8 GHz, to determine if the sample contains an $Fe^{3+}$ atom (i.e., an iron atom with a valence of 3+) in an $Al_2O_3$ matrix.

Further, in conventional EPR, the resonator is tuned to critical coupling where there is minimal (if any) reflected signal from the resonator. Measurements are made by monitoring the change in reflection at only one frequency[7], the resonant frequency, as a magnetic field is systematically varied in strength. Such devices also use a lock-in and take the derivative of a detected change for maximum sensitivity. This method requires either a standard or a method that measures the Q value at zero field and then uses several approximations to quantify the results, such as a sample's paramagnetic concentration.

[7] In contrast, embodiments of the disclosure scan over a range of frequencies, with all points besides the resonant frequency providing significant reflection values.

Although potentially this method can be accurate, it requires the use of a standard with a known paramagnetic concentration to make the quantitative determinations. However, with this conventional measurement method, it is often not possible to infer the sample's magnetic loss tangent with a single measurement even with a reference standard.

As disclosed and/or described, in one or more of the embodiments, the resonator response comes from the metal enclosure, resonator chamber, and sample. In contrast, conventional EPR does not use a dielectric resonator inside the chamber, but instead creates a resonance from within the chamber walls. It also uses a system that operates entirely at microwave frequencies including components that include a microwave source, waveguides, attenuator, phase shifter, circulator, detector, amplifier, directional coupler, phase-sensitive lock-in amplifier, modulation source, an electromagnet, modulation coil, and control electronics that can include a digitizer and computer.

As disclosed and/or described, embodiments incorporate multiple features and components that together enable the detection and/or measurement of paramagnetic species in a sample and provide this capability in a handheld form factor. This enables portability and usage in multiple settings that would not be possible with conventional measurement devices.

As further non-limiting examples, embodiments may utilize a cylindrical or ring dielectric with a relatively large dielectric constant and a small loss tangent enclosed in a sample or resonator chamber. For the intended measurements, the material used in the resonator chamber preferably has little (or no) active electron paramagnetic resonance species under the measurement conditions. This can be achieved by using a dielectric with no (or a minimum) concentration of paramagnetic native and impurity defect centers and/or having paramagnetic species with little (or no) observable response under the measurement conditions due to a sufficiently short spin-lifetime.

Further, the use of a high dielectric constant material, preferably one at or above a dielectric constant value of 50, enables a significant size reduction (e.g., a size of <2") in the resonator so that it can operate at a desired frequency of, for example, 2 GHZ. The use of a relatively high dielectric constant dielectric confines the electric field to (mostly) the dielectric, enabling a small dielectric to enclosure distance while minimizing near-field microwave losses, and thus maintaining a high quality (Q) factor. Holes added for sample insertion and/or light source entry in select locations can still allow minimal radiation losses as well, still facilitating a high quality value.

In one embodiment, the microwave dielectric resonator material is high-dielectric (~100) low loss tangent (<0.0005) and sufficiently low magnetic loss tangent (<0.0005) $TiO_2$ materials in ceramic form. Examples include a cylindrical shape with an outer diameter (OD) of ~1" and height of ~0.25", or a ring shape with an OD of ~1", an inner diameter (ID) of <0.5", and a height of ~0.25". In either configuration, the material includes a doping of Al of order 0.02 mol % with loss tangents less than 0.00015, and preferably less than 0.0001.

To compensate for paramagnetic defects (even though Ti is valence 2 and Al is valence 3), the inventors used ultra-high purity 99.99%+ pure (metals basis) rutile $TiO_2$ reactants to make a ceramic with a minimal number of paramagnetic centers, including the commonly encountered iron and even native defects. This level of purity was not known to be available commercially before the development of the disclosed device.

Other possible materials for use in constructing or fabricating the resonator are the low-loss tangent tungsten bronze ceramics with rare-earth elements that have minimal paramagnetic loss at and near room temperature. These include but are not limited to those available from Trans-tech (the series 7300), having a dielectric constant of 75 and near 0 temperature coefficient, including and in addition to Ba—Sm—Ti—Ta—O or Nd—Ti—Ce—Al/Ga—Ba—Sm—Ti—Ti-Al-O compounds.

Regarding the microwave frequencies used by the disclosed vector network analyzer for performing the measurements (typically approximately 2 GHz), in many conventional devices 10 GHz is traditionally favored for most applications. This is because for detection or measurement of a relatively low concentration, 10 GHz (3 cm wavelength) offers the highest sensitivity, at a reasonable cost ($100,000-$1,500,000), with reasonable size samples, and because the required large, heavy (100-1500 pounds) electromagnets are available and affordable to researchers. Above that frequency (e.g., at 35, 90 GHz), the magnets become significantly more expensive.

In contrast, embodiments operate using a microwave frequency range of 1.5-3 GHz because it enables the use of permanent magnets and provides a longer microwave penetration depth (on the order of 0.5-1 cm) into the sample, and because water and many liquids have much lower (parasitic) electric loss at these frequencies. This may be important for measuring free radicals in food and biological specimens. In some use cases, one can compensate for the lower sensitivity at these frequencies compared to measurements at higher frequencies arising from the Boltzmann factor, (which impacts the population distribution between the separated energy levels) by using a larger sample size (assuming an appropriate permanent magnet design).

In some embodiments, the sample and dielectric may be held with rigid supports to minimize the influence of any relative motion of the parts within the enclosure, thus minimizing the possible introduction of alteration in the microwave response. In such embodiments, the parts are selected to have minimal or no active paramagnetic species under the measurement condition, as well as sufficient rigidity and springiness to create tension to hold the part in place and serve as a form of shock absorber.

One example embodiment used PLA plastic fabricated with 3D printing, which resulted in a material with a sufficiently small paramagnetic resonance response. Other plastics and resin composites that may be suitable include (but are not limited to) Form labs Ridgid 4000, Gray pro, Clear, or Tough 2000, although these materials exhibit a higher active paramagnetic signal at room temperature.

In some embodiments, the described configuration allows for the introduction of additional ports without a significant drop in Q to allow sample introduction and removal, including an entrance through the center of the enclosed metallic chamber enclosure top and/or bottom for the sample insertion tool, and the inclusion of an optical ultraviolet or visible light source at the top and/or bottom cavity enclosure circumference to excite electrons in the sample, thereby generating paramagnetic species. If present, the UV/visible light source is used to generate paramagnetic species in the sample and does not influence the microwave source or resonator response directly.

In some embodiments, the quality factor (Q) is measured using the disclosed vector network analyzer (VNA) circuit on a single printed circuit board and comprised of 2 microwave generating phase-lock loop circuits whose output is down-converted to an inter-frequency (IF) signal and then processed using compact circuitry that includes a microwave mixer, directional coupler, amplifier, switches, and an analog-to-digital converter. As disclosed, the magnetic loss tangent of the sample and its paramagnetic concentration can be inferred from the change in quality factor when a resonance-inducing magnetic field is applied.

Measurements as a function of frequency through or near the resonance condition can be done in reflection (S11 measurement) and/or transmission (S12 measurement) mode, although the reflection mode is preferred due to the simplicity of design it enables, with only one microwave electric-field or magnetic-field coupling probe being required. The measured loss tangent can be determined from the Smith chart by fitting the circle using the standard method described in the book "Q Factor Measurements Using MATLAB" (D. Kajfez, Artech House Inc. New York (2011)), or from the method, one of which is described above, to infer S11 and then use the equation $Q=f/\Delta f$ for the $S_{11}$ resonance peak, where f is the resonant frequency and $\Delta f$ is the difference in the frequency between the 3 dB points which are located at ±90 degrees from the resonant frequency on the Smith chart. The microwave reflection is measured at or near critical coupling and the change in response due to the magnetic field is proportional to the paramagnetic concentration of the sample, which is typically expressed in units of the number of paramagnetic species per cubic centimeter.

As mentioned, in one embodiment, a vector network analyzer is used to measure the reflection values of the resonator chamber and sample, and of a reference standard to determine the reflection scattering parameter S11 as a function of frequency through the resonator's resonance value. The reference standard can be a short circuit or other means to create a signal that has a reflection coefficient of unity or near-unity. From this, the quality factor (Q) of the combined resonator chamber and sample can be determined.

In one embodiment and example use case, the disclosed device is used to measure approximately 730 data points of the reflection signal as a function of time for both the resonator (the chamber and sample) and the standard (having a reflection coefficient of unity or near-unity) at each frequency. This is followed by determining the relative amplitude and phase of the reflected signal, and then determining the S11 values (i.e., the relative reflection values) of the order of 50 different frequencies. These are fit to a Smith chart, and this approach provides a significant reduction in signal-to-noise because of signal averaging. This can be significant, as random variables are known to decrease a measured signal-to-noise by a factor proportional to the square root of the number of samples taken; for example, the signal-to-noise of 730 data points is reduced by a factor of approximately 27.

In one embodiment, the dielectric is in a ring geometry, and a magnetic-field coupling probe is used, which results in efficient excitation of the TE01δ dielectric resonant mode. This results in a mode with the electric field and magnetic field largely separated. A relatively high dielectric constant material in a ring configuration is used for the dielectric to concentrate the electric field within the dielectric and minimize the electric field in the sample space (analogously to a coil where the electric field is confined in the conductive ring). This minimizes losses from electric dipoles (which absorb energy from water and foodstuff, as in a microwave oven) that degrade the Q of the cavity, the signal-to-noise ratio, and thus the sensitivity of the instrument. For example, with a 0.5" hole, it allows over a millimeter of liquid with minimal (<10%) loss in Q and thus only a minor decrease in sensitivity from this factor.

In this embodiment, a magnetic-field coupling probe in the shape of a loop is used to excite the TE01δ dielectric resonant mode. In one embodiment, the magnetic-field coupling probe and connectors and wires are fabricated from non-ferromagnetic materials such as stainless steel, brass or select beryllium copper alloys (in some cases with gold plating) to minimize the influence of magnetoresistance and other changes in the resonator microwave response from internal and external parts. The standard commercial microwave component plating process that utilizes a nickel adhesion layer below the gold is not used. This is because ferromagnetic materials can exhibit relatively large magnetoresistance and potentially significant Hall voltages that produce an unwanted background (i.e., noise) in the presence of a static or near-static magnetic field. As mentioned, the coil design functions to excite the fundamental mode of the dielectric resonator so that it concentrates the microwave magnetic field in and centrally located in and above the hole in the open region of the resonator.

In some embodiments, the size and position of the permanent magnet(s) are optimized to maximize the overlap between the microwave magnetic field, the tangential DC magnetic field, and the sample volume. This maximizes the fill factor, the signal-to-noise ratio of the measurement, and thus improves the sensitivity of the measurement.

Although the operation of the device using a ~2 GHz frequency with a compact resonator of <5 cm (and preferably at <3.8 cm) outer diameter and height of <3.5 cm (and preferably of <2.5 cm) results in a decrease in sensitivity of a factor of 5 for a given sample volume over the most commonly-used ~10 GHz EPR resonator, this factor is more than compensated for by allowing a much higher sample volume and resulting enhanced fill factor, and thus, a beneficial net gain in an optimized configuration, with a beneficial decrease in the electric losses in liquids and many other materials that might be used as samples.

In this regard, some materials have a much smaller electric field loss tangent at 2 GHz than at 10 GHz. For example, the fractional reduction is 3 times for water and 5 times for dielectrics used in microwave circuits for 2 GHz as opposed to 10 GHz. The resulting beneficial increase in the microwave penetration depth in foodstuff and biological material to typically 8-15 mm for 2 GHz is considerably deeper than that for 10 GHz radiation. This increases the amount of detectable paramagnetic species and improves the ability to detect and quantify smaller paramagnetic concentrations.

The disclosed combination of features facilitates the use of a relatively small permanent magnet to attain the electron paramagnetic resonant condition. Since the required magnetic field scales with the microwave frequency, the magnetic field for a 2 GHz system can be 5 times smaller than for the most-often-used frequency of 10 GHz. For example, a field of ~714 G (gauss) rather than 3568 G can be used to flip the spin at the free electron value of g=2.00023 at 2 GHz. Peaks near this value are labeled the "g=2" peak and range from ~680-740 G because of factors such as spin-orbit coupling interactions. Similarly, the g=4 and g=6 peaks from a molecule such as deoxyhemoglobin fall at ~357 and 178 G, rather than at ~1784 and 892 G.

The reduction in feasible magnetic field strength allows for the use of relatively small (<2.5 cm diameter, <1 cm thick) high-performance magnets such as the neodymium iron boron (NdFeB), samarium cobalt (SmCo), ceramic iron-based, and alnico varieties to enable a relatively large volume of the sample volume to be under the resonance condition.

Further, in some embodiments, the use of an asymmetric geometry such that the dielectric, sample and coupling probe are nearer the permanent magnet's (if one permanent magnet is used) or one of the permanent magnets' position (if more than one permanent magnet is used), resulting in an enhanced volume in which the sample can be in the paramagnetic resonance condition. This in combination with the sample lying in a relatively high microwave magnetic field (creating a large fill factor) facilitates a large paramagnetic electron resonance signal. This arrangement also results in an enhanced Q from minimal near field losses at the other end from the top cavity sides and wall. Further, by moving the permanent magnet using the disclosed shaft and servo, the magnetic field can be used to scan from the absence of resonance through the resonance condition.

Figure 2C:
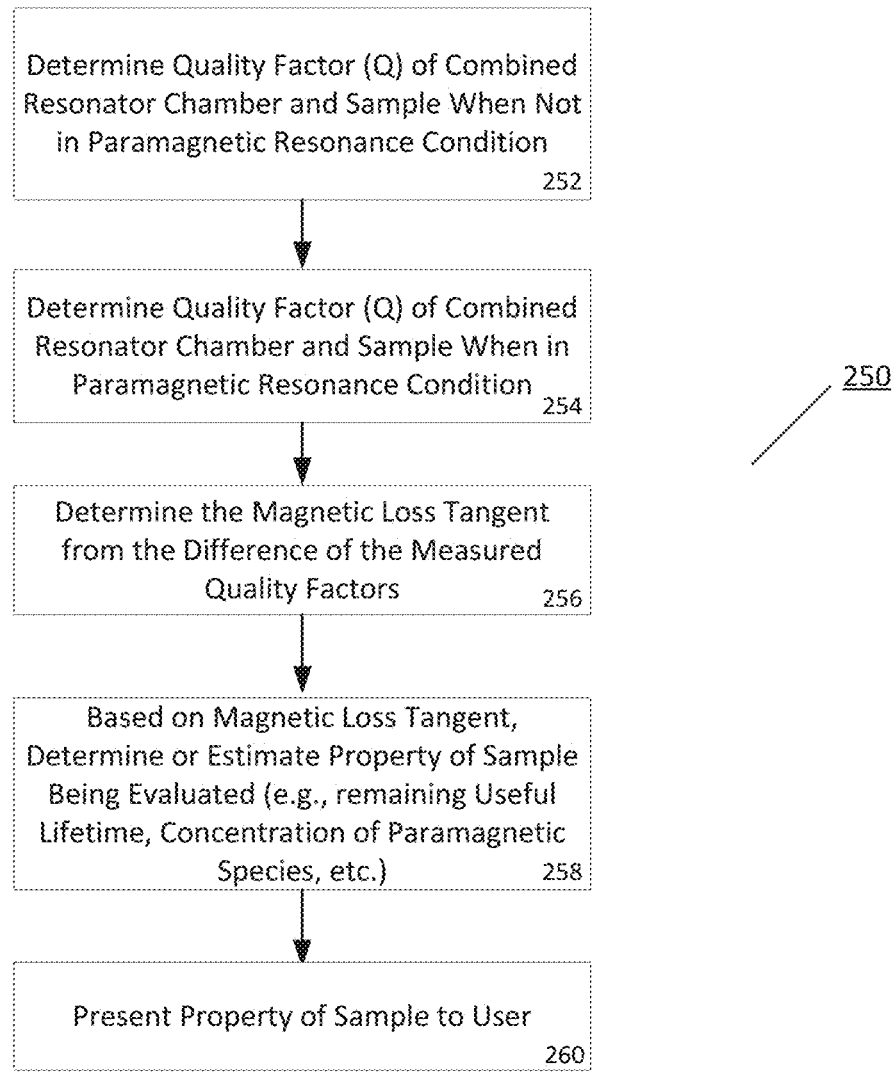
FIG. 2(c) is a flowchart or flow diagram illustrating a method, process, operation, or set of functions to enable a user to determine the concentration of paramagnetic species in a sample, in accordance with some embodiments.

FIG. 2(c) is a flowchart or flow diagram illustrating a method, process, operation, or set of functions 250 to enable a user to determine the concentration of paramagnetic species in a sample, in accordance with some embodiments. In one embodiment, a method, process, or set of steps, stages, operations, or functions may include:

Determining a Quality Factor (Q) of a Combined Resonator Chamber and Sample When Not in a Paramagnetic Resonance Condition (as suggested by step or stage 252);
Where the Q value is determined using a vector network analyzer (VNA), and where this may comprise selecting a set of RF frequencies and corresponding LO (local oscillator) frequencies that scan through all or part of the combined resonance chamber and sample paramagnetic resonance condition;
Using the resonator and reference data to determine the S11 values as a function of frequency and from that determine the quality factor (Q) of the resonator (e.g., using a Smith chart);
Determine the Quality Factor (Q) of the Combined Resonator Chamber and Sample When in a Paramagnetic Resonance Condition (as suggested by step or stage 254);
Determine the Magnetic Loss Tangent from the Difference of the Measured Quality Factors (as suggested by step or stage 256);
In some embodiments, this determination of the Magnetic Loss Tangent from the Difference of the Measured Quality Factors (as suggested by step or stage 256, and everywhere else mentioned throughout this specification) may comprise a more complicated relationship than a subtraction operation and/or may include consideration of the sample geometry; Such sample geometry considerations may include, for example in some embodiments, the dimensions of the sample and/or a fill factor as defined above.
Based on the Magnetic Loss Tangent, Determine or Estimate Property of Sample Being Evaluated (e.g., remaining Useful Lifetime, Concentration of Paramagnetic Species, etc.) (as suggested by step or stage 258);
In one embodiment, this may include accessing a database or library of data representing a similar substance as the sample, its known or estimated concentration of paramagnetic species (or a specific species) as a function of time, and an indication of a threshold value or time at which such sample becomes unusable or unsafe (or possesses other undesirable characteristic).
Present Property of Sample to User (as suggested by step or stage 260);
In one embodiment, this may be performed by generating a display on a user interface of a device that is implementing the described steps or stages.

As disclosed and/or described herein, in one embodiment, a process for measuring S11, determining a value for Q, determining a loss tangent and from that a magnetic loss tangent, and from that a species concentration may include one or more of the following steps or stages:
Place sample into resonator chamber (where the chamber contains the disclosed dielectric, dielectric holders, and magnetic-field coupling probe, among other components or elements);
Adjust the position of one or more permanent or the current in one or more electromagnets to cause the sample to not be in a paramagnetic resonance condition;
Measure the S11 magnitude and phase values and use a Smith chart to determine the Q factor of the combined resonator comprised of the sample plus chamber;
Adjust the position of the one or more permanent or the current in one or more electromagnets to cause the sample to be in a paramagnetic resonance condition;
Measure the S11 magnitude and phase values and use a Smith chart to determine the Q factor of combined resonator comprised of the sample plus chamber;
For a well-characterized resonator, from the change in Q factors in the two measurement situations combined with information about the sample geometry, determine the magnetic loss tangent of the sample. Here, a well-characterized resonator refers to one which has also been measured without a sample in place;

From the magnetic loss tangent of the sample along with previously obtained calibration data or known EPR relaxation times (i.e., T1 and/or T2), determine the paramagnetic species concentration or the desired sample property (such as the usable lifetime of a foodstuff);

It is preferable to use the magnetic loss tangent over just the change in Q since the magnetic loss tangent is an inherent property of a sample (i.e., it does not depend on sample's shape or size). When the magnetic loss tangent is determined, direct evaluation of the material's properties can be established independent of its size, shape, or measurement configuration. This also allows direct comparison to other samples measured in other electron paramagnetic resonance instruments and can improve the accuracy and reliability of the measurement results; or From the change in Q factors in the two measurement situations along with previously obtained calibration data, determine the paramagnetic species concentration or a sample's property.

In one embodiment, a microprocessor or microcontroller in the disclosed device may be programmed with a set of computer-executable instructions, that when executed, cause the device to perform one or more steps, stages, processes, operations, or functions. These steps, stages, processes, operations, or functions may include those to enable a user to interact with the device to perform a measurement of a sample, and for the device to perform the measurement and present the results to the user.

Figure 2D:
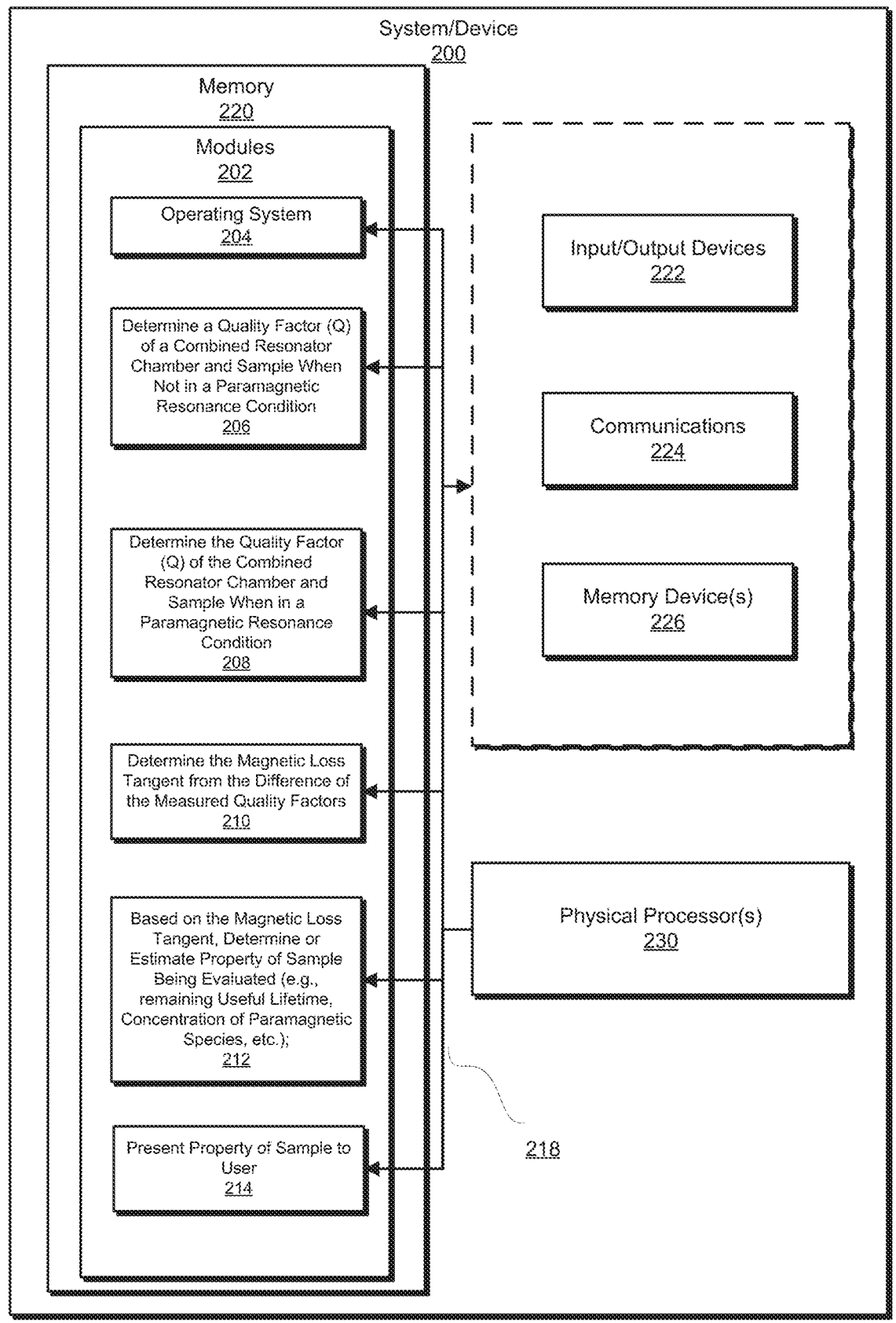
FIG. 2(d) is a diagram illustrating elements or components that may be present in a computing device or other form of client configured to implement a method, process, function, or operation in accordance with some embodiments.

As a non-limiting example, FIG. 2(d) is a diagram illustrating elements or components that may be present in a device or system 200 configured to implement a method, process, function, or operation in accordance with some embodiments. As noted, in some embodiments, the disclosed and/or described system and methods may be implemented in the form of an apparatus that includes a processing element (i.e., a processor) and a set of executable instructions stored in (or on) a non-transitory computer-readable memory or data storage component. The executable instructions may be part of a software application and arranged into a software architecture.

In general, an embodiment of the disclosure may be implemented using a set of software instructions that are designed to be executed by one or more suitably programmed processing elements (such as a GPU, TPU, CPU, QPU, state machine, microprocessor, processor, controller, or other computing device). In a complex application or system such instructions are typically arranged into "modules" with each such module typically performing a specific task, process, function, or operation. The entire set of modules may be controlled or coordinated in their operation by an operating system (OS) or other form of organizational platform.

The application modules and/or sub-modules may include any suitable computer-executable code or set of instructions (e.g., as would be executed by a suitably programmed processor, microprocessor, or CPU), such as computer-executable code corresponding to a programming language. For example, programming language source code may be compiled into computer-executable code. Alternatively, or in addition, the programming language may be an interpreted programming language such as a scripting language.

As mentioned, each module may contain instructions which when executed by a programmed processor or co-processors cause an apparatus (such as a client device or server) to perform the specific function or functions.

As shown in FIG. 2, system 200 may represent a client, or other form of computing or data processing device. Modules 202 each contain a set of executable instructions, where when the set of instructions is executed by a suitable electronic processor (such as that indicated in the figure by "Physical Processor(s) 230"), system (or device) 200 operates to perform a specific process, operation, function, or method. Modules 202 may contain one or more sets of instructions for performing a method or function described with reference to the Figures, and the descriptions of the functions and operations provided in the specification. The modules may include those illustrated but may also include a greater number or fewer number than those illustrated. Further, the modules or the computer-executable instructions that are contained in a module or modules may be executed by the same processor or by more than a single processor.

Modules 202 are stored in a memory 220, which typically includes an Operating System module 204 that contains instructions used (among other functions) to access and control the execution of the instructions contained in other modules. The modules 202 in memory 220 are accessed for purposes of transferring data and executing instructions by use of a "bus" or communications line 218, which also serves to permit processor(s) 230 to communicate with the modules for purposes of accessing and executing a set of instructions. Bus or communications line 218 also permits processor(s) 230 to interact with other elements of system 200, such as input or output devices 222, communications elements 224 for exchanging data and information with devices external to system 200, and additional memory devices 226.

Each application module or sub-module may correspond to a specific function, method, process, or operation that is implemented by the module or sub-module. Each module or sub-module may contain a set of computer-executable instructions that when executed by a programmed processor or co-processors cause the processor or co-processors (or a device or devices in which they are contained) to perform the specific function, method, process, or operation.

With reference to FIG. 2(d), in some embodiments, the implemented steps, stages, elements, components, functions, methods, processes, or operations may include those used to perform one or more aspects of the disclosed and/or described system and methods, such as for determining if a specific toxin is present in a sample of food. In some embodiments, this may include execution of a set of computer-executable instructions that cause an embodiment of the disclosed and/or described device to:

By the User
   powers the device,
   inserts the sample,
   chooses the type of sample being measured, such as fish, chicken, coffee, or a beverage (as non-limiting examples);

Presses the "start measurement button on the screen";

The VNA is programmed and operable to source the appropriate frequencies through the microwave circuit to measure the reflection values of the resonator (i.e., the sample and containing chamber) and a reference signal to determine the reflection scattering parameter (S11) as a function of frequency through the resonator's resonance condition or value. The reference signal can be a short circuit or other means to create a signal that has a reflection coefficient of unity or near-unity. S11 is determined by taking the ratio of the measured reflection from device under test to that of a reference signal that reflects as close to 100% as possible at each frequency;

Determine Quality Factor (Q) of a Combined Resonator Chamber and Sample When Not in a Paramagnetic Resonance Condition (as suggested by module 206);
  Where the Q value is determined using the vector network analyzer (VNA), and selecting a set of RF frequencies and corresponding LO (local oscillator) frequencies that scan through all or part of the combined resonance chamber and sample paramagnetic resonance condition;
  Using the resonator and reference data to determine the S11 values as a function of frequency and from that determine the quality factor (Q) of the resonator (e.g., using a Smith chart);

Determine the Quality Factor (Q) of the Combined Resonator Chamber and Sample When in a Paramagnetic Resonance Condition (module 208);

Determine the Magnetic Loss Tangent from the Difference of the Measured Quality Factors (module 210);
  In some embodiments, this determination of the Magnetic Loss Tangent from the Difference of the Measured Quality Factors (as suggested by module 210, and everywhere else mentioned throughout this specification) may comprise a more complicated relationship than a subtraction operation and/or may include consideration of the sample geometry; Such sample geometry considerations may include, for example in some embodiments, the dimensions of the sample and/or a fill factor as defined above.

Based on the Magnetic Loss Tangent, Determine or Estimate Property of Sample Being Evaluated (e.g., remaining Useful Lifetime, Concentration of Paramagnetic Species, etc.) (module 212);
  In one embodiment, this may include accessing a database or library of data representing a similar substance as the sample, its known or estimated concentration of paramagnetic species (or a specific species) as a function of time, and an indication of a threshold value or time at which such sample becomes unusable or unsafe (or possesses other undesirable characteristic); and Present Property of Sample to User (module 214);
  In one embodiment, this may be performed by generating a display on a user interface of a device that is implementing the described steps or stages.

In some uses of the disclosed and/or described device, this may include the following user interactions with a display or user interface of the device:

Turn the unit on by moving the power switch to "on";

Place the sample into the sample insertion tool and insert it into the large, circular hole in the casing, thereby placing the sample into the resonant chamber;

Choose the type of product to be measured from a set of illustrative icons or symbols, such as fish, chicken, coffee, beverage, or other;

Once a type of sample to be tested is chosen, press the button or select the user interface element that says "test";

Once the test process is completed, the evaluation will be displayed. For fish and chicken, it may indicate "very fresh", "fresh", "edible", or "non-edible". For coffee, it may indicate "over roasted", "slightly over roasted", "ideal roasting", "slightly under roasted" or "under roasted". For a beverage, it may indicate either "safe" or "dangerous";

If desired, the user can press the setting button on the main menu so that they can record which user is making the measurement, the time and date and results of the measurement. There may also be an option to access a diagnostic feature to determine if the electronics and interface are working up to their original specification.

Figure 2E:
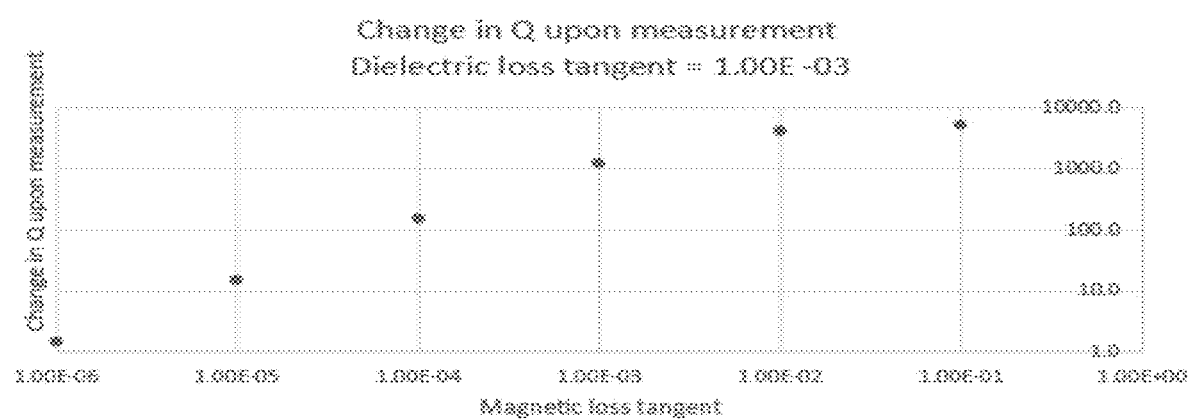
FIG. 2(e) is a graph illustrating an electromagnetic simulation (i.e., using a Maxwell equation solver) that may be used to convert the measured Q to a magnetic loss tangent value.

FIG. 2(e) is a graph illustrating an electromagnetic simulation (i.e., using a Maxwell equation solver, HFSS, sold by Ansys) that may be used to determine a sample's magnetic loss tangent from the measured change in the Q between a non-resonant and resonant electron paramagnetic resonance condition. For the simulation, a "lossy" cylindrical sample with dimensions of 0.5" outer diameter and 0.25" high was used in the simulations. The term "lossy" refers to a sample with many dipoles so that its electric loss tangent is 0.001. The value for the electric loss tangent can be inferred from the measured quality factor in the non-resonant condition when using a well-characterized resonator and the magnitude used here is typical for a food sample with a moderate water content.

The graph illustrates an example of how the measured change in Q can be used to determine a value for a sample's magnetic loss tangent. In the simulation, the sample's magnetic loss tangent is set to zero in the non-resonant condition and the quality factor from the simulation of the microwave fields and resulting losses is noted. The sample's magnetic loss tangent is then set to the various values in the graph, the simulations are carried out, and the resulting quality factors are noted. From that value, the change in quality factor is inferred and tabulated. The graph (or a similar tool) then enables a user to determine the magnetic loss tangent from the change in Q for this experimental configuration and sample.

Figure 2F:
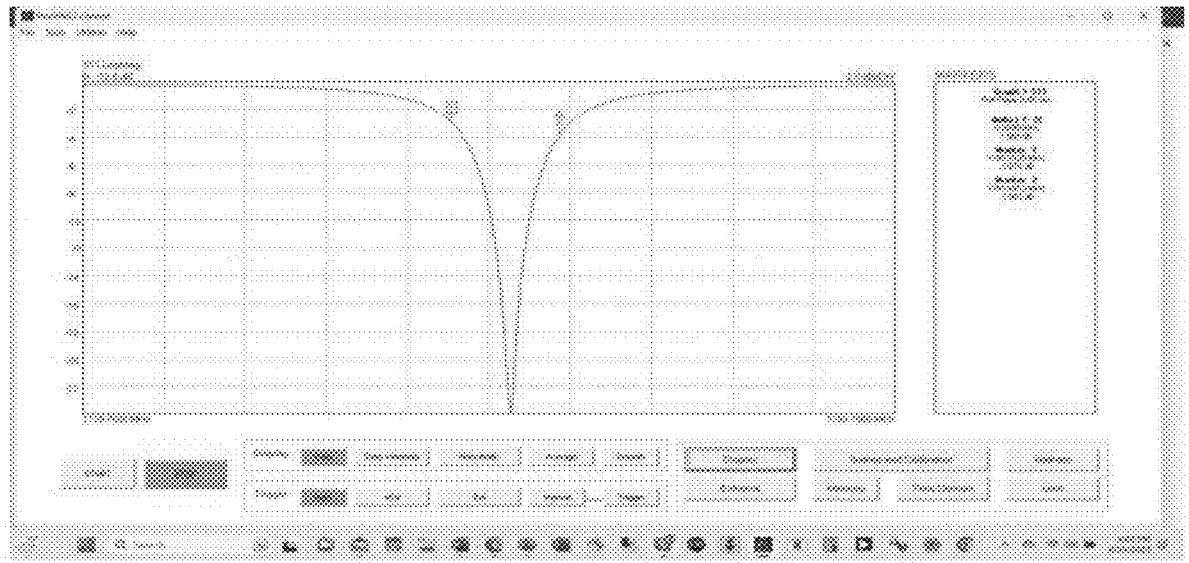
FIGS. 2(f) to 2(h) are graphs illustrating a process for using measured S11 magnitude and phase values to make a Smith chart, and from that to determine the quality factor (Q) of a resonator.
Figure 2G:
Figure 2H:
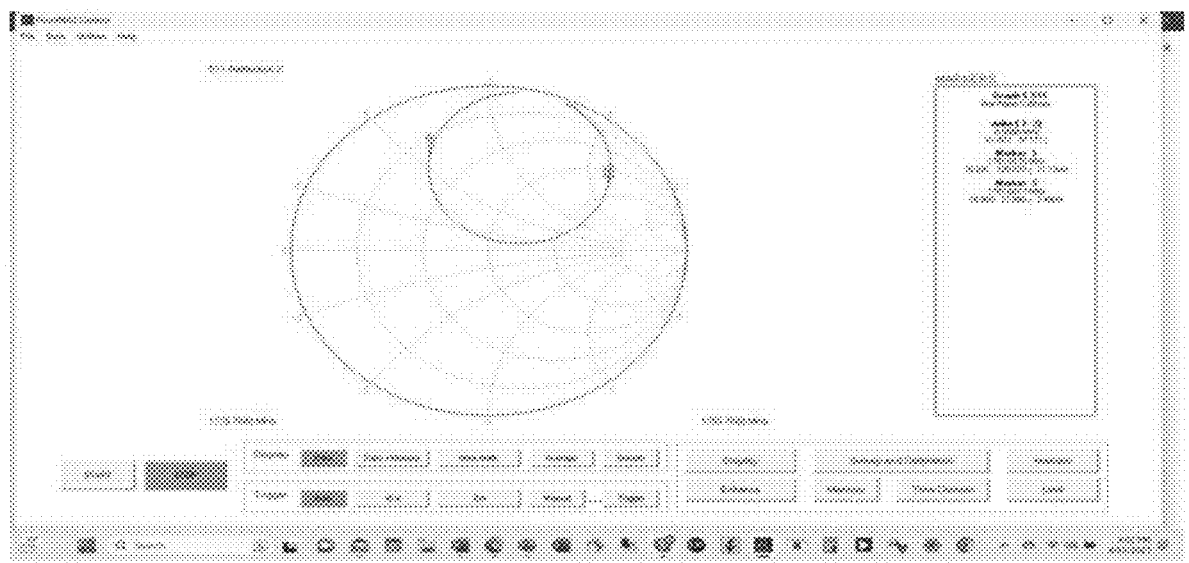

FIGS. 2(f) to 2(h) are graphs illustrating a process for using measured S11 magnitude and phase values to make a Smith chart, and from that to determine the quality factor (Q) of a resonator.

As a non-limiting example, in one embodiment, a process for determining the Q factor may include the following steps or stages:

Measure S11 of a resonator comprised of a chamber, ring dielectric, and sample as a function of frequency, for example at 51 points over 5 MHz, though the resonance condition. Plot all of the S11 points versus frequency (as illustrated in FIG. 2(f));
  for the magnitude one will observe a "V" shaped curve where the beginning and end of the "V" are not in resonance and S11 will have a value near 1 and thus 0 dB (i.e., almost 100% reflection). At resonance, the S11 magnitude is at the minimum (e.g., 0.01). If the resonator is critically coupled, then the S11 magnitude will be zero (i.e., zero reflection, thus minus infinity and all is transmitted) under ideal conditions and at or near the noise floor in practical devices. At close to critical coupling, the value will be small (e.g., 0.01, i.e., −40 dB);

The phase should shift by roughly 180 degrees, with zero shift (i.e., completely resistive) at resonance (as illustrated in FIG. 2(g));

When plotted on a Smith chart, one can determine the Q factor of the chamber, ring dielectric, and sample by fitting the curve of combined sample plus chamber or by finding the two 3 dB points that are located ±90 degrees from the apex of the circle Q factor (as illustrated in FIG. 2(h)).

Potential use cases and benefits of the disclosed and/or described approach may include the following users and contexts, and provide an informed answer to the indicated question(s):

Wildfire fighters: Am I breathing in cancer-causing smoke? Is it imperative that I wear my breathing apparatus?

For those with compromised respiratory and immune systems: Is the air safe? If I go outside, should I wear a particle mask?

Sushi restaurants: Is my product safe? Has the fish gone bad?

Fish and meat retailers: Is the meat fresh? Was the transportation from the fishery or packing house refrigerated all the time? Was there a power outage, causing unsafe temperature excursions in my freezer that I do not know about?

Fast food restaurants: Where my food products left out too long or mishandled? Have the cold cuts spoiled? Is the cheese still edible?

For food producers: Have I added too little or too many antioxidants? What is the optimal amount for the desired food lifetime?

For surgery units: Is the wound healing properly? Is it receiving adequate amounts of oxygen?

For athletes: Is my level of oxygen depletion affecting my performance? Is my injury producing dangerously high levels of methaemoglobin?

For everyone: Do I have too much or too much iron in the form of ferritin in my body? Such conditions telegraph the possibility that you are suffering from such conditions as anemia, hyperthyroidism, liver disease, high levels of inflammation in the body or bacterial infection and indicate that you need medical attention.

For those at risk of cancer: Are my levels of ROS (reactive oxygen species), ferritin or methaemoglobin changing? Should I see a doctor immediately?

For those concerned about melanoma and other skin diseases: Are my moles and other trouble spots on my skin changing with time? If so, what does my dermatologist recommend?

For food producers who use irradiation to kill bacteria and other organism: Did the foodstuff receive the targeted irradiation dosage?

For those exposed to irradiation: What cumulative dosage have I been exposed to?

For petroleum refiners: Does the crude oil have even trace amounts of catalyst-degrading vanadium in the petroleum oils that I am refining?

Embodiments of the disclosed and/or described handheld electron paramagnetic resonant (EPR) instrument are able to measure the paramagnetic concentration of a wide variety of practical substances, ranging from food and beverages to biological specimens and solid-state electronic materials. The disclosed device is portable and performs a measurement faster than commonly used techniques to quantify this parameter, including methods that use vibrating sample magnetometers and other existing electron paramagnetic resonance spectrometers. In the former case, a temperature scan of the sample's magnetization is performed. In the latter case, a scan of the magnetic field is performed while monitoring the sample's reflection at a fixed microwave frequency, followed by an analysis involving the subtraction of the ever-present background and subsequent double integration of the differentiated signal. Both these conventional approaches necessarily require more complex measurement devices and computational resources to achieve a desired level of accuracy.

In contrast, with the disclosed device, measurements are made with one or more magnets that create an electron paramagnetic resonant field or fields in the sample space so that the electron paramagnetic resonance response of a selected single or group of EPR transitions from a chemical species of interest are simultaneously excited. The difference in the quality factor of the resonator chamber and sample between the measurements in a resonance condition and out of a resonance condition is used to infer the free radical concentration for the chemical component or species of interest. In some cases, to differentiate between different species, additional single or groups of transitions can be measured, and the magnitude and ratio of the measured values can be used to quantify the paramagnetic concentration of one or more species at levels of (or better than) parts per million.

For measurements made using the disclosed device, the background signal, defined as the difference in the quality factor between the magnetic fields used during the measurements, should be small or absent, with a maximum value preferably on the order of 1 part in ~2500 or better. To achieve these conditions, methods were used by the inventors to (1) develop and acquire ultra-pure/paramagnetic-free insulators and fixturing material with the desired mechanical and microwave properties (since commercial material was not previously available) and (2) use specialized microwave cavity enclosures, coaxial wires, connectors, and magnetic-field coupling probe which do not contain even trace amounts of ferromagnetic regions and/or layers.

To design a portable instrument, the inventors developed a design to achieve up to 800 G, with gradient fields spanning a range from +5 G to +75 G over areas on the order of 0.5"×0.5"×0.25". One or more coin-sized magnets with weights of as little as 5 grams were chosen. In one example, embodiments utilize disc- and ring-shaped ceramic (NdFeB) permanent magnets.

To realize electron paramagnetic resonance at those fields, a resonator with a resonant frequency of <~2.5 GHz was used. In one example, a dielectric resonator in the shape of a ring was used. This allows the design to have the sample placed in the central axis (the hole) such that one or more permanent magnets can be moved a small distance from a position in which the sample is exposed to the resonance conditions and to a position where it is not. Proper choice of the material and resonator geometry ensures that the sample is exposed to the desired relatively high microwave magnetic field that maximizes the electron paramagnetic resonance response and a minimal microwave electric field, which minimizes degradation of the quality factor, and thus sensitivity, from the large electric dipole induced losses typically present in foodstuff, biological specimens, liquids, and other materials. To minimize the electric field at the sample location and achieve a resonator on the order of 1.5" outer diameter, embodiments used a dielectric constant for the microwave dielectric resonator of a value >50 and preferably with a value >~100.

To characterize the microwave response and determine the quality factor, embodiments measured the complex valued reflected signal components (i.e., phase and amplitude) of the resonator chamber and sample as a function of frequency with a miniature VNA (vector network analyzer) on a printed circuit board. The designed VNA used 2 microwave generators produced by phase-lock loops which are down-converted to an inter-frequency (IF) signal and then processed using circuitry that includes a microwave mixer, directional coupler, amplifier, switches, and an analog-to-digital (ADC) converter. The VNA makes measurements of the amplitude and phase of the reflection of a microwave signal from the resonator with the sample enclosed and a reference standard that has unity or near unity reflectance characteristics as the frequencies are swept thought the resonator's resonance. The ratio of the magnitude of the values represents the magnitude of each S11 value and the difference in phase represents the phase of each S11 value. The resulting S11 values are then fit using a method using a Smith Chart, as described by the Kajvez reference.

As disclosed and/or described, embodiments incorporate a dielectric in the metallic enclosure chamber that acts as a dielectric resonator. The dielectric (and sample if present) is scanned with a magnetic field and the Q factors are determined and recorded. In one embodiment, the Q factors for measurements under the electron paramagnetic resonant condition and not under the electron paramagnetic field resonant condition are each inverted, and these values are subtracted to obtain an estimate of the sample's magnetic loss tangent. When converting this magnetic loss tangent value to a concentration, the conversion may be impacted by the spin-lifetime, which is a function of temperature. This can introduce an error when deriving a concentration directly from the magnetic loss tangent under some measurement conditions.

The determination of the free-radical concentration can allow for an accurate prediction of the time remaining in the useable or safe lifetime of a product. In some embodiments, this is may be based on a series of measurements made over time, because as the measurement or evaluation time approaches a threshold value that has previously proven to constitute spoiled food, an investigator can predict with some certainty that a sample will no longer be useable or safe at the time of measurement or at some time in the future.

In some use cases, to determine and/or evaluate the presence of a species of interest in water or food, one may need a standard or example with a known concentration (and a threshold value of a time from production or preparation at which the sample becomes unsafe or unusable).

In some cases, an estimated $T_1$ lifetime of a species may be inferred from the linewidth of the peak in the electron paramagnetic resonant versus magnetic field and application of the Heisenberg uncertainty principle when the sample is in an unsaturated condition and the resonant peak or peaks are homogeneously broadened.

As a non-limiting example of a process for determining a Q value for a sample, one may use the equation $1/Q_{meas}=1/Q_{(cav+dielectric)}+1/Q_{sample}$. This is followed by determining the $1/Q_{sample}$ value and using that as an index to a set of previously obtained data/measurements on free radical concentration for different species, and/or a time for a sample becoming unsafe or unusable.

However, additional information may be required to determine the paramagnetic concentration from the sample's magnetic loss tangent when a standard or set of previous measurements for a species or type of sample is not available. While the paramagnetic concentration is proportional to the magnetic loss tangent, knowledge of the sample's $T_2$ (termed the spin-spin or transverse relaxation time) and/or $T_1$ (termed the spin-lattice or longitudinal relaxation time) in combination with the Bloch equation are required to infer the paramagnetic concentration from the magnetic loss tangent.

In some cases, the lifetime of a paramagnetic species is available in the literature and may be used. When this is not the case, those skilled in the art of electron paramagnetic resonance can perform continuous wave (CW), pulsed and/or Fourier transform EPR measurements and subsequent analysis to determine one or both parameters. For example, under homogeneously broadened and unsaturated conditions using continuous wave EPR measurements, $T_2$ can be determined directly from the width of the peak in the spectra that plots the electron paramagnetic signal measured by the EPR system versus magnetic field. Furthermore, for unsaturated conditions (the focus of the measurements when using an embodiment of the disclosed device), one can assume that $T_2 \ll T_1$, in which case the Bloch equations simplify, and a reasonably accurate determination of the paramagnetic concentration can be inferred from only the knowledge of the magnetic loss tangent and $T_2$. Note that $T_1$ involves energy losses to or from the system's energy degrees of freedom (which also includes the lattice), while $T_2$ involves energy exchange within the spin system.

Embodiments as disclosed and/or described herein above can be implemented in the form of control logic using computer software in a modular or integrated manner. Based on the disclosure and teachings provided herein, a person of ordinary skill in the art will know and appreciate other ways and/or methods to implement one or more embodiments using hardware and a combination of hardware and software.

This disclosure includes the following embodiments and clauses:

1. A device that can determine the chemical properties of a sample, comprising:
   a dielectric resonator comprised of a dielectric with a dielectric constant between 65 and 140 and a metallic chamber enclosure wherein the metallic chamber enclosure diameter is less than 1.6 times the diameter of the dielectric, both having an opening through which a sample may be inserted and/or placed;
   a source of a microwave signal configured to introduce a continuous-wave (CW) microwave signal into the dielectric resonator at a frequency in the range of 1.0 to 4.0 GHZ;
   a magnetic-field coupling probe in the shape of a loop used to excite the resonant modes of the dielectric resonator;
   one or more components configured to adjust a magnetic field by positioning one or more permanent magnets and the current from zero, one, or more electromagnets to create a condition in which the sample is not in a paramagnetic resonant condition and to adjust the magnetic field by positioning one or more permanent magnets and the current from zero, one, or more electromagnets to create a condition in which the sample is in a paramagnetic resonant condition;
   a component configured to measure reflectance as the microwave frequency is scanned through the resonance of the structure containing the sample, the dielectric and metallic chamber enclosure to determine a quality factor when the sample is not in a paramagnetic resonant condition and to measure the reflectance as the microwave frequency is scanned through the resonance of the structure containing the sample, the dielectric and metallic chamber enclosure to determine a quality factor when the sample is in a paramagnetic resonant condition; and a component configured to determine a characteristic property of the sample from the measurements of the quality factors.

2. The device of clause 1, wherein the component configured to measure the reflectance is a vector network analyzer that measures the magnitude and phase of the reflectance signal.

3. The device of clause 1, wherein the device has dimensions of less than 12"×12"×12".

4. The device of clause 1, wherein the device having dimensions of less than 8"×8"×5".

5. The device of clause 1, wherein the resonator is less than 1.5" in diameter and 0.95" high and has an unloaded quality factor over 4,000 and a critically coupled quality factor over 2,000.

6. The device of clause 1, wherein the characteristic of the sample is a concentration of one or more paramagnetic species in the sample.

7. A method using the measured quality factor values from the device of clause 1, wherein the magnetic loss tangent of the sample is determined using analytic equations.

8. A method using the measured quality factor values from the device of clause 1, wherein the magnetic loss tangent of the sample is determined using computer simulations.

9. A method using the device of clause 1, wherein a particular characteristic of the sample can be determined from the inferred magnetic loss tangent and a library or database containing data regarding one or more categories of samples, with each category associated with one or more measured magnetic loss tangent of paramagnetic samples and one or more chemical properties of the sample.

10. A method using the device of clause 1, comprising the steps of
measuring Q values;
from the measured Q values, determining magnetic loss tangent;
from magnetic loss tangent, accessing a library to determine a chemical property of the sample.

11. The device of clause 1, wherein the characteristic of the sample is a characteristic selected from the group of characteristics comprising:
the safety of the sample for consumption or use;
freshness of the sample, wherein the sample comprises food, and wherein the freshness further comprises a determination of when the food is deemed undesirable to eat; and
a interval of time elapsed since preparation of the sample.

12. The device of clause 1, wherein measuring the quality factor of the combined sample and resonant chamber when not in a paramagnetic resonant conditions and when the combined sample and resonant chamber are in a paramagnetic resonant condition further comprises:
using a vector network analyzer to generate near-monochromatic microwave frequency radiation at a set of frequencies that range through all or part of the combined resonance chamber and sample paramagnetic resonance condition;
directing the microwave radiation generated at the selected frequencies to the combined sample and resonator chamber or to a reference component;
using the resonator and reference component magnitude and phase reflection data to determine the S11 values as a function of frequency; and
using the determined S11 values to determine the quality factor.

13. The device of clause 1, wherein measuring the quality factor of the combined sample and resonant chamber when not in a paramagnetic resonant conditions and when the combined sample and resonant chamber are in a paramagnetic resonant condition further comprises:
using a spectrum analyzer to generate near-monochromatic microwave frequency radiation at a set of frequencies that range through all or part of the combined resonance chamber and sample paramagnetic resonance condition;
directing the microwave radiation generated at the selected frequencies to the combined sample and resonator chamber or to a reference component;
using the resonator and reference component magnitude reflection data to determine the S11 values as a function of frequency; and
using the determined S11 values to determine the quality factor.

14. The device of clause 1, wherein the sample is one selected from the group comprising fish, meat, fruit, nuts, milk, blood, and air.

15. The device of clause 1, wherein the one or more permanent magnets are used to produce the DC magnetic field and are any one or more selected from the group of magnets comprising: ceramic iron-based magnets, samarium cobalt-based magnets, Alnico magnets, Nd-based magnets, or any other type of permanent magnet.

16. The device of clause 1, wherein the dielectric and dielectric holders confined within the resonant chamber enclosure both have a paramagnetic concentration below $10^{18}/cm^3$.

17. The device of clause 1, wherein the dielectric and dielectric holders confined within the resonant chamber enclosure both have a paramagnetic concentration below $10^{15}/cm^3$.

18. The device of clause 1, wherein the dielectric is made from $TiO_2$ ceramics which contain additives totaling less than 5 atomic percent.

19. The device of clause 1, wherein the dielectric holder is made from polylactic acid (PLA).

20. The device of clause 1, wherein the dielectric holders are made from plastics.

21. The device of clause 1, further using a magnetic-field coupling probe and one or more coaxial connectors and wires, some or all of which are made completely from non-magnetic materials.

22. The device of clause 1, further comprising a source of irradiation configured to generate unpaired electrons in the sample.

Any of the software components, processes or functions disclosed and/or described herein may be implemented as software code to be executed by a processor using a suitable computer language such as Python, Java, JavaScript, C++, or Perl using conventional or object-oriented techniques. The software code may be stored as a series of instructions, or commands in (or on) a non-transitory computer-readable medium, such as a random-access memory (RAM), a read only memory (ROM), a magnetic medium such as a hard-drive, or an optical medium such as a CD-ROM. In this context, a non-transitory computer-readable medium is a medium suitable for the storage of data or an instruction set aside from a transitory waveform. Such computer readable medium may reside on or within a single computational apparatus and may be present on or within different computational apparatuses within a system or network.

According to one example implementation, the term processing element or processor, as used herein, may be a central processing unit (CPU), or conceptualized as a CPU (such as a virtual machine). In this example implementation, the CPU or a device in which the CPU is incorporated may be coupled, connected, and/or in communication with one or more peripheral devices, such as a display. In another example implementation, the processing element or processor may be incorporated into a mobile computing device, such as a smartphone or tablet computer.

The non-transitory computer-readable storage medium referred to herein may include a number of physical drive units, such as a redundant array of independent disks (RAID), a flash memory, a USB flash drive, an external hard disk drive, thumb drive, pen drive, key drive, a High-Density Digital Versatile Disc (HD-DV D) optical disc drive, an internal hard disk drive, a Blu-Ray optical disc drive, or a Holographic Digital Data Storage (HDDS) optical disc drive, synchronous dynamic random access memory (SDRAM), or similar device or form of memory based on similar technologies. Such computer-readable storage media allow the processing element or processor to access computer-executable process steps or application programs, stored on removable and non-removable memory media, to off-load data from a device or to upload data to a device. As mentioned, with regards to the embodiments disclosed and/or described herein, a non-transitory computer-readable medium may include almost any structure, technology, or method apart from a transitory waveform or similar medium.

One or more embodiments of the disclosure are described herein with reference to block diagrams of systems, and/or to flowcharts or flow diagrams of functions, operations, processes, or methods. One or more blocks of the block diagrams, or one or more stages or steps of the flowcharts or flow diagrams, and combinations of blocks in the block diagrams and stages or steps of the flowcharts or flow diagrams, respectively, may be implemented by computer-executable program instructions. Note that in some embodiments, one or more of the blocks, or stages or steps may not need to be performed in the order presented or may not need to be performed at all.

The computer-executable program instructions may be loaded onto a general-purpose computer, a special purpose computer, a processor, or other programmable data processing apparatus to produce a specific example of a machine, such that the instructions that are executed by the computer, processor, or other programmable data processing apparatus create means for implementing one or more of the functions, operations, processes, or methods disclosed and/or described herein. The computer-executable program instructions may be stored in (or on) a computer-readable memory that can direct a computer or other programmable data processing apparatus to function in a specific manner, such that the instructions stored in (or on) the computer-readable memory produce an article of manufacture including instruction means that implement one or more of the functions, operations, processes, or methods disclosed and/or described herein.

While embodiments of the disclosure have been described in connection with what is presently considered to be the most practical implementation, the disclosed and/or described approach is not limited to those embodiments. Instead, the disclosed and/or described embodiments are intended to cover various modifications and equivalent arrangements included within the scope of the appended claims. Although specific terms are employed herein, they are used in a generic and descriptive sense and not for purposes of limitation.

This written description includes one or more examples describing implementations of the disclosed approach to enable a person skilled in the art to practice one or more embodiments of the disclosure, including making and using a device or system and performing an incorporated method. The patentable scope of embodiments of the disclosure is defined in the claims, and may include other examples that occur to those skilled in the art. Such other examples are intended to be within the scope of the claims if they have structural and/or functional elements that do not differ from the literal language of the claims, or if they include structural and/or functional elements with insubstantial differences from the literal language of the claims.

All references, including publications, patent applications, and patents, cited herein are hereby incorporated by reference to the same extent as if each reference were individually and specifically indicated to be incorporated by reference and/or were set forth in its entirety herein.

The use of the terms "a" and "an" and "the" and similar references in the specification and in the claims are to be construed to cover both the singular and the plural, unless otherwise indicated herein or clearly contradicted by context. The terms "having," "including," "containing" and similar references in the specification and in the claims are to be construed as open-ended terms (e.g., meaning "including, but not limited to,") unless otherwise noted.

Recitation of ranges of values herein are intended to serve as a shorthand method of referring individually to each separate value inclusively falling within the range, unless otherwise indicated herein, and each separate value is incorporated into the specification as if it were individually recited herein. Methods or processes disclosed and/or described herein may be performed in any suitable order unless otherwise indicated herein or clearly contradicted by context. The use of examples, or exemplary language (e.g., "such as") herein is intended to illuminate embodiments of the disclosure and does not pose a limitation to the scope of the claims unless otherwise indicated. No language in the specification should be construed as indicating any non-claimed element as essential to each embodiment of the disclosure.

As used herein (i.e., the claims, figures, and specification), the term "or" is used inclusively to refer to items in the alternative and in combination.

Different arrangements of the components or operations illustrated in the drawings or disclosed and/or described herein, as well as components and steps not shown or explicitly described may be possible. Similarly, some features and sub-combinations may be useful and may be implemented without reference to other features and sub-combinations. Embodiments of the disclosure are described for illustrative and not for restrictive purposes, and alternative embodiments may be apparent. Accordingly, the disclosure is not limited to the embodiments described and/or illustrated in the drawings, and other embodiments and modifications may be made without departing from the scope of the claims.

That which is claimed is:

1. A device configured to determine chemical properties of a sample, comprising:
    a dielectric resonator comprising a dielectric with a dielectric constant between 65 and 140 and a metallic chamber enclosure wherein a diameter of the metallic chamber enclosure is less than 1.6 times a diameter of the dielectric, both having an opening configured for a sample to be inserted therethrough;

a source of a microwave signal configured to introduce a continuous-wave (CW) microwave signal into the dielectric resonator at a frequency in the range of 1.0 to 4.0 GHZ;

a magnetic-field coupling probe comprising a loop used to excite resonant modes of the dielectric resonator;

one or more components configured to adjust a value of a magnetic field generated within the sample by one or more permanent magnets by positioning the one or more permanent magnets to create a condition in which the sample is not in a paramagnetic resonant condition and to adjust the magnetic field generated within the sample by the one or more permanent magnets by positioning the one or more permanent magnets to create a condition in which the sample is in a paramagnetic resonant condition;

a component configured to measure reflectance as a microwave frequency is scanned over a frequency range through a resonance of a structure containing the sample, the dielectric and the metallic chamber enclosure to determine a quality factor when the sample is not in a paramagnetic resonant condition and to measure the reflectance as the microwave frequency is scanned through the resonance of the structure containing the sample, the dielectric and metallic chamber enclosure to determine a quality factor when the sample is in a paramagnetic resonant condition; and the component configured to measure reflectance is further configured to determine the chemical properties of the sample from the determined quality factors.

2. The device of claim 1, wherein the component configured to measure the reflectance comprises vector network analyzer configured to measure a magnitude and phase of the reflectance signal.

3. The device of claim 1, wherein the device has dimensions of less than 12"×12"×12".

4. The device of claim 1, wherein the device having dimensions of less than 8"×8"×5".

5. The device of claim 1, wherein the resonator is less than 1.5" in diameter and 0.95" high and has an unloaded quality factor over 4.000 and a critically coupled quality factor over 2,000.

6. The device of claim 1, wherein the characteristic of the sample is a concentration of one or more paramagnetic species in the sample.

7. The device of claim 1, wherein the component configured to measure reflectance comprises a processor programmed to use a difference between the determined quality factor values, wherein a magnetic loss tangent of the sample is determined using analytic equations.

8. The device of claim 1, wherein the component configured to measure reflectance comprises a processor programmed to use a difference between the determined quality factor values, wherein a magnetic loss tangent of the sample is determined using computer simulations.

9. The device of claim 1, wherein a chemical property of the sample is determined from a determined magnetic loss tangent and a library or database containing data regarding one or more categories of samples, with each category associated with one or more determined magnetic loss tangent of paramagnetic samples and one or more chemical properties of the sample.

10. The device of claim 1, wherein the component configured to measure reflectance comprises a processor programmed to:

determine a magnetic loss tangent from the determined quality factors;

access a library and compare the magnetic loss tangent to the library to determine a chemical property of the sample.

11. The device of claim 1, wherein the chemical property of the sample comprises at least one of the following characteristics:

a safety of the sample for consumption or use;

a freshness of the sample, wherein the sample comprises food, and wherein the freshness further comprises a determination of when the food is deemed undesirable to eat; and an interval of time elapsed since preparation of the sample.

12. The device of claim 1, wherein the component configured to measure reflectance to determine the quality factor of the resonance of the structure when not in a paramagnetic resonant condition is determined and the quality factor of the resonance of the structure when in a paramagnetic resonant condition comprises a processor programmed to:

use a vector network analyzer to generate near-monochromatic microwave frequency radiation at a set of frequencies that range through all or part of the structure paramagnetic resonance condition;

direct the microwave radiation generated at the selected frequencies to the structure or to a reference component;

use the resonator and reference component magnitude and phase reflection data to determine S11 values as a function of frequency; and use the determined S11 values to determine the quality factor.

13. The device of claim 1, wherein the component configured to measure reflectance to determine the quality factor of the resonance of the structure when not in a paramagnetic resonant condition and the quality factor of the resonance of the structure when the in a paramagnetic resonant condition comprises a processor programmed to:

use a spectrum analyzer to generate near-monochromatic microwave frequency radiation at a set of frequencies that range through all or part of the structure paramagnetic resonance condition;

direct the microwave radiation generated at the selected frequencies to the structure or to a reference component;

use the resonator and reference component magnitude reflection data to determine S11 values as a function of frequency; and use the determined S11 values to determine the quality factor.

14. The device of claim 1, wherein the sample is one selected from the group consisting of: fish, meat, fruit, nuts, milk, blood, and air.

15. The device of claim 1, wherein the one or more permanent magnets are used to produce a DC magnetic field and are selected from the group of magnets consisting of: ceramic iron-based magnets, samarium cobalt-based magnets, Alnico magnets, and Nd-based magnets.

16. The device of claim 1, wherein the dielectric resonator comprises dielectric holders confined within the metallic chamber enclosure, and the dielectric and dielectric holders both have a paramagnetic concentration below $10^{18}/cm^3$.

17. The device of claim 1, wherein the dielectric resonator comprises dielectric holders confined within the metallic chamber enclosure, and the dielectric and dielectric holders both have a paramagnetic concentration below $10^{15}/cm^3$.

18. The device of claim 1, wherein the dielectric is made from $TiO_2$ ceramics which contain additives totaling less than 5 atomic percent.

19. The device of claim 1, wherein the dielectric resonator comprises a dielectric holder confined within the metallic chamber enclosure, and the dielectric holder is made from polylactic acid (PLA).

20. The device of claim 1, wherein the dielectric resonator comprises a dielectric holder confined within the metallic chamber enclosure, and the dielectric holder is made from plastics.

21. The device of claim 1, wherein at least a portion of the a magnetic-field coupling probe and one or more coaxial connectors and wires are made completely from non-magnetic materials.

22. The device of claim 1, further comprising a source of irradiation configured to generate unpaired electrons in the sample.

23. The device of claim 1, further comprising at least one electromagnet wherein the one or more components configured to adjust a value of the magnetic field is configured to position the one or more permanent magnets and a current from the at least one electromagnet to adjust the value of the magnetic field.

* * * * *